United States Patent
Riber et al.

(10) Patent No.: US 11,795,204 B2
(45) Date of Patent: *Oct. 24, 2023

(54) GLUCAGON ANALOGUES

(71) Applicant: Zealand Pharma A/S, Søborg (DK)

(72) Inventors: Ditte Riber, Brønshøj (DK); Lise Giehm, Frederiksberg (DK)

(73) Assignee: Zealand Pharma A/S, Søborg (DK)

( * ) Notice: Subject to any disclaimer, the term of this patent is extended or adjusted under 35 U.S.C. 154(b) by 167 days.

This patent is subject to a terminal disclaimer.

(21) Appl. No.: 16/566,992

(22) Filed: Sep. 11, 2019

(65) Prior Publication Data

US 2020/0207825 A1    Jul. 2, 2020

Related U.S. Application Data

(63) Continuation of application No. 14/417,074, filed as application No. PCT/EP2013/065519 on Jul. 23, 2013, now Pat. No. 10,442,847.

(60) Provisional application No. 61/785,611, filed on Mar. 14, 2013, provisional application No. 61/674,706, filed on Jul. 23, 2012.

(51) Int. Cl.
| | |
|---|---|
| C07K 14/605 | (2006.01) |
| A61K 38/26 | (2006.01) |
| A61K 38/00 | (2006.01) |

(52) U.S. Cl.
CPC ............ *C07K 14/605* (2013.01); *A61K 38/26* (2013.01); *A61K 38/00* (2013.01)

(58) Field of Classification Search
CPC ....... C07K 14/605; A61K 38/26; A61K 38/00
See application file for complete search history.

(56) References Cited

U.S. PATENT DOCUMENTS

| | | |
|---|---|---|
| 4,288,627 A | 9/1981 | Kubicek |
| 5,118,666 A | 6/1992 | Habener |
| 5,120,712 A | 6/1992 | Habener |
| 5,424,286 A | 6/1995 | Eng |
| 5,512,549 A | 4/1996 | Chen et al. |
| 5,523,449 A | 6/1996 | Prasad et al. |
| 5,545,618 A | 8/1996 | Buckley et al. |
| 5,614,492 A | 3/1997 | Habener |
| 5,631,224 A | 5/1997 | Efendic et al. |
| 5,670,360 A | 9/1997 | Thorens |
| 5,795,861 A | 8/1998 | Kolterman et al. |
| 5,846,747 A | 12/1998 | Thorens et al. |
| 5,846,937 A | 12/1998 | Drucker |
| 6,006,753 A | 12/1999 | Efendic |
| 6,051,689 A | 4/2000 | Thorens |
| 6,110,703 A | 8/2000 | Egel-Mitani et al. |
| 6,114,304 A | 9/2000 | Kolterman et al. |
| 6,136,784 A | 10/2000 | L'Italien et al. |
| 6,191,102 B1 | 2/2001 | DiMarchi et al. |
| 6,268,343 B1 | 7/2001 | Knudsen et al. |
| 6,271,241 B1 | 8/2001 | DeSimone et al. |
| 6,277,819 B1 | 8/2001 | Efendic |
| 6,284,725 B1 | 9/2001 | Coolidge et al. |
| 6,329,336 B1 | 12/2001 | Bridon et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,410,508 B1 | 6/2002 | Isales et al. |
| 6,410,511 B2 | 6/2002 | L'Italien et al. |
| 6,451,974 B1 | 9/2002 | Hansen |
| 6,458,924 B2 | 10/2002 | Knudsen et al. |
| 6,506,724 B1 | 1/2003 | Hiles et al. |
| 6,528,486 B1 | 3/2003 | Larsen et al. |
| 6,703,359 B1 | 3/2004 | Young et al. |
| 6,767,887 B1 | 7/2004 | Hoffmann et al. |
| 6,858,576 B1 | 2/2005 | Young et al. |
| 6,872,700 B1 | 3/2005 | Young et al. |
| 6,902,744 B1 | 6/2005 | Kolterman et al. |
| 6,924,264 B1 | 8/2005 | Prickett et al. |
| 6,956,026 B2 | 10/2005 | Beeley et al. |
| 6,989,366 B2 | 1/2006 | Beeley et al. |
| 7,056,734 B1 | 6/2006 | Egan et al. |
| 7,115,569 B2 | 10/2006 | Beeley et al. |
| 7,138,375 B2 | 11/2006 | Beeley et al. |
| 7,153,825 B2 | 12/2006 | Young et al. |
| 7,157,555 B1 | 1/2007 | Beeley et al. |
| 7,220,721 B1 | 5/2007 | Beeley et al. |
| 7,223,725 B1 | 5/2007 | Beeley et al. |
| 7,226,990 B2 | 6/2007 | Knudsen et al. |
| 7,235,627 B2 | 6/2007 | Knudson et al. |
| 7,297,761 B2 | 11/2007 | Beeley et al. |

(Continued)

FOREIGN PATENT DOCUMENTS

| | | |
|---|---|---|
| AU | 3247799 A | 9/1999 |
| AU | 2008326324 A1 | 5/2009 |

(Continued)

OTHER PUBLICATIONS

Unson et al., Jl. Biol. Chem. 273/17, 10308-10312 (1998) (supplied in Mar. 30, 2017 IDS) (Year: 1998).*
Hruby et al., Curr. Med. Chem—Imm., Endoc. & Metab. Agents, 199-215 (2001) (supplied in Mar. 30, 2017 IDS) (Year: 2001).*
Carbone et al., Cancer Research 64, 5518-5524, Aug. 1, 2004 (Year: 2004).*
Mayo Clinic Glucagon, 11 pages, downloaded Sep. 20, 2022 (Year: 2022).*
Chabenne et al., Jl Diabetes Sci and Tech, 4:6, 1322-1331 (2010) (Year: 2010).*
Pospisilik et al., Regulatory Peptides, 96 (2001) 133-141, (Year: 2001).*

(Continued)

*Primary Examiner* — Melissa L Fisher
*Assistant Examiner* — Joseph Fischer
(74) *Attorney, Agent, or Firm* — Clark & Elbing LLP

(57) ABSTRACT

The present invention relates to glucagon analogues and their medical use, for example in the treatment of hypoglycaemia. In particular, the present invention relates to stable glucagon analogues suitable for use in a liquid formulation.

11 Claims, 1 Drawing Sheet
Specification includes a Sequence Listing.

(56) References Cited

U.S. PATENT DOCUMENTS

| | | |
|---|---|---|
| 7,348,404 B2 | 3/2008 | Holm et al. |
| 7,399,489 B2 | 7/2008 | Kolterman et al. |
| 7,407,932 B2 | 8/2008 | Young et al. |
| 7,419,952 B2 | 9/2008 | Beeley et al. |
| 7,442,680 B2 | 10/2008 | Young et al. |
| 7,452,858 B2 | 11/2008 | Hiles et al. |
| 7,521,423 B2 | 4/2009 | Young et al. |
| 7,544,657 B2 | 6/2009 | Ebbehoj et al. |
| 7,601,691 B2 | 10/2009 | Bridon et al. |
| 7,608,692 B2 | 10/2009 | Prickett et al. |
| 7,623,530 B2 | 11/2009 | Hurtta |
| 7,683,030 B2 | 3/2010 | Prickett et al. |
| 7,691,963 B2 | 4/2010 | Prickett et al. |
| 7,696,161 B2 | 4/2010 | Beeley et al. |
| 7,700,549 B2 | 4/2010 | Beeley et al. |
| 7,741,269 B2 | 6/2010 | Young et al. |
| 7,858,740 B2 | 12/2010 | Beeley et al. |
| 7,928,065 B2 | 4/2011 | Young et al. |
| 7,935,786 B2 | 5/2011 | Larsen |
| 7,994,122 B2 | 8/2011 | Riber et al. |
| 8,026,210 B2 | 9/2011 | Young et al. |
| 8,057,822 B2 | 11/2011 | Prickett et al. |
| 8,097,698 B2 | 1/2012 | Knudsen et al. |
| 8,263,550 B2 | 9/2012 | Beeley et al. |
| 8,288,338 B2 | 10/2012 | Young et al. |
| 8,445,647 B2 | 5/2013 | Prickett et al. |
| 8,642,540 B2 | 2/2014 | Meier et al. |
| 8,642,541 B2 | 2/2014 | Meier et al. |
| 8,642,727 B2 | 2/2014 | Larsen et al. |
| 8,680,049 B2 | 3/2014 | Meier et al. |
| 8,685,919 B2 | 4/2014 | Meier et al. |
| 9,089,538 B2 | 7/2015 | Neerup et al. |
| 9,156,901 B2 | 10/2015 | Riber et al. |
| 9,169,310 B2 | 10/2015 | Riber et al. |
| 9,180,169 B2 | 11/2015 | Tolborg et al. |
| 9,403,894 B2 | 8/2016 | Meier et al. |
| 9,453,064 B2 | 9/2016 | Just et al. |
| 9,649,362 B2 | 5/2017 | Neerup et al. |
| 9,896,495 B2 | 2/2018 | Riber et al. |
| 9,969,787 B2 | 5/2018 | Just et al. |
| 9,975,939 B2 | 5/2018 | Tolborg et al. |
| 9,988,429 B2 | 6/2018 | Riber et al. |
| 10,004,786 B2 | 6/2018 | Riber et al. |
| 10,093,713 B2 | 10/2018 | Shelton et al. |
| 10,100,097 B2 | 10/2018 | Just et al. |
| 2002/0137666 A1 | 9/2002 | Beeley et al. |
| 2004/0106547 A1 | 6/2004 | Larsen et al. |
| 2005/0070469 A1 | 3/2005 | Bloom et al. |
| 2006/0057137 A1 | 3/2006 | Steiness |
| 2006/0194719 A1 | 8/2006 | Ebbehoj et al. |
| 2006/0293232 A1 | 12/2006 | Levy et al. |
| 2007/0111940 A1 | 5/2007 | Larsen et al. |
| 2009/0088369 A1 | 4/2009 | Steiness |
| 2010/0099601 A1 | 4/2010 | Weiss |
| 2010/0190701 A1 | 7/2010 | Day et al. |
| 2010/0240883 A1 | 9/2010 | Wu et al. |
| 2011/0144008 A1 | 6/2011 | Larsen et al. |
| 2011/0230397 A1 | 9/2011 | Carriero et al. |
| 2011/0245165 A1 | 10/2011 | Larsen et al. |
| 2011/0286981 A1 | 11/2011 | Meier et al. |
| 2011/0286982 A1 | 11/2011 | Meier et al. |
| 2011/0293586 A1 | 12/2011 | Meier et al. |
| 2011/0293587 A1 | 12/2011 | Meier et al. |
| 2011/0312878 A1 | 12/2011 | Larsen |
| 2012/0178670 A1 | 7/2012 | Riber et al. |
| 2013/0053304 A1 | 2/2013 | Wang et al. |
| 2013/0064822 A1 | 3/2013 | Ye et al. |
| 2013/0157929 A1 | 6/2013 | Riber et al. |
| 2013/0157935 A1 | 6/2013 | Meier et al. |
| 2013/0157953 A1 | 6/2013 | Petersen et al. |
| 2013/0316941 A1 | 11/2013 | Hamprecht et al. |
| 2014/0011733 A1 | 1/2014 | Fosgerau et al. |
| 2014/0080757 A1 | 3/2014 | Tolborg et al. |
| 2014/0127174 A1 | 5/2014 | Meier et al. |
| 2014/0127175 A1 | 5/2014 | Meier et al. |
| 2014/0187483 A1 | 7/2014 | Steiness |
| 2014/0336356 A1 | 11/2014 | Larsen et al. |
| 2015/0080295 A1 | 3/2015 | Meier et al. |
| 2015/0111817 A1 | 4/2015 | Riber et al. |
| 2015/0111826 A1 | 4/2015 | Riber et al. |
| 2015/0210744 A1 | 7/2015 | Riber et al. |
| 2015/0299281 A1 | 10/2015 | Just et al. |
| 2015/0322130 A1 | 11/2015 | DiMarchi et al. |
| 2015/0376257 A1 | 12/2015 | Riber et al. |
| 2016/0000883 A1 | 1/2016 | Fosgerau et al. |
| 2016/0009777 A1 | 1/2016 | Tolborg et al. |
| 2016/0120951 A1 | 5/2016 | Riber et al. |
| 2016/0304576 A1 | 10/2016 | Meier et al. |
| 2016/0347813 A1 | 12/2016 | Hamprecht et al. |
| 2018/0141990 A1 | 5/2018 | Riber et al. |

FOREIGN PATENT DOCUMENTS

| | | |
|---|---|---|
| CN | 101519446 A | 9/2009 |
| DE | 102008003566 A1 | 7/2009 |
| DE | 102008003568 A1 | 7/2009 |
| EP | 0082731 A1 | 6/1983 |
| EP | 1076066 A1 | 2/2001 |
| EP | 1196444 B1 | 6/2003 |
| EP | 1329458 A2 | 7/2003 |
| EP | 1421950 A1 | 5/2004 |
| EP | 2025684 A1 | 2/2009 |
| EP | 2028192 A1 | 2/2009 |
| EP | 1525219 B1 | 5/2009 |
| EP | 2112161 A2 | 10/2009 |
| EP | 2565205 A1 | 3/2013 |
| JP | 2011-524418 A | 9/2011 |
| JP | 2012-511900 A | 5/2012 |
| WO | WO-91/11457 A1 | 8/1991 |
| WO | WO-91/17243 A1 | 11/1991 |
| WO | WO-93/18786 A1 | 9/1993 |
| WO | WO-95/05848 A1 | 3/1995 |
| WO | WO-97/46584 A1 | 12/1997 |
| WO | WO-98/05351 A1 | 2/1998 |
| WO | WO-98/08531 A1 | 3/1998 |
| WO | WO-98/08871 A1 | 3/1998 |
| WO | WO-98/08873 A1 | 3/1998 |
| WO | WO-98/11125 A1 | 3/1998 |
| WO | WO-98/11126 A1 | 3/1998 |
| WO | WO-98/19698 A1 | 5/1998 |
| WO | WO-98/22577 A1 | 5/1998 |
| WO | WO-98/30231 A1 | 7/1998 |
| WO | WO-98/35033 A1 | 8/1998 |
| WO | WO-98/39022 A1 | 9/1998 |
| WO | WO-98/50351 A1 | 11/1998 |
| WO | WO-99/07404 A1 | 2/1999 |
| WO | WO-99/25727 A2 | 5/1999 |
| WO | WO-99/25728 A1 | 5/1999 |
| WO | WO-99/40788 A1 | 8/1999 |
| WO | WO-99/43707 A1 | 9/1999 |
| WO | WO-99/43708 A1 | 9/1999 |
| WO | WO-99/46283 A1 | 9/1999 |
| WO | WO-99/49788 A1 | 10/1999 |
| WO | WO-99/64060 A1 | 12/1999 |
| WO | WO-00/09666 A2 | 2/2000 |
| WO | WO-00/34331 A2 | 6/2000 |
| WO | WO-00/41546 A2 | 7/2000 |
| WO | WO-00/41548 A2 | 7/2000 |
| WO | WO-00/55119 A1 | 9/2000 |
| WO | WO-00/55184 A1 | 9/2000 |
| WO | WO-00/66629 A1 | 11/2000 |
| WO | WO-00/73331 A2 | 12/2000 |
| WO | WO-01/04156 A1 | 1/2001 |
| WO | WO-01/32158 A2 | 5/2001 |
| WO | WO-02/34285 A2 | 5/2002 |
| WO | WO-03/022304 A1 | 3/2003 |
| WO | WO-03/053339 A2 | 7/2003 |
| WO | WO-03/053460 A1 | 7/2003 |
| WO | WO-2004/005342 A1 | 1/2004 |
| WO | WO-2004/062685 A2 | 7/2004 |
| WO | WO-2004/096854 A2 | 11/2004 |
| WO | WO-2005/072045 A2 | 8/2005 |
| WO | WO-2006/051110 A2 | 5/2006 |
| WO | WO-2006/097537 A2 | 9/2006 |

(56) References Cited

FOREIGN PATENT DOCUMENTS

| WO | WO-2006/121860 A2 | 11/2006 | |
|---|---|---|---|
| WO | WO-2006/134340 A2 | 12/2006 | |
| WO | WO-2007/024899 A2 | 3/2007 | |
| WO | WO-2007/056362 A2 | 5/2007 | |
| WO | WO-2007/081824 A2 | 7/2007 | |
| WO | WO-2007/095737 A1 | 8/2007 | |
| WO | WO-2007/100535 A2 | 9/2007 | |
| WO | WO-2008/010101 A2 | 1/2008 | |
| WO | WO-2008/071010 A1 | 6/2008 | |
| WO | WO-2008/071972 A1 | 6/2008 | |
| WO | WO-2008/086086 A2 | 7/2008 | |
| WO | WO-2008/101017 A2 | 8/2008 | |
| WO | WO-2008/152403 A1 | 12/2008 | |
| WO | WO-2008/155257 A1 | 12/2008 | |
| WO | WO-2009/067636 A2 | 5/2009 | |
| WO | WO-2009/077737 A2 | 6/2009 | |
| WO | WO-2009/087081 A2 | 7/2009 | |
| WO | WO-2009/087082 A2 | 7/2009 | |
| WO | WO-2009/129250 A2 | 10/2009 | |
| WO | WO-2009/132129 A2 | 10/2009 | |
| WO | WO-2009/152128 A1 | 12/2009 | |
| WO | WO-2009/155257 A1 | 12/2009 | |
| WO | WO-2009/155258 A2 | 12/2009 | |
| WO | WO-2010/002283 A9 | 1/2010 | |
| WO | WO-2010/011439 A2 | 1/2010 | |
| WO | WO-2010/014946 A2 | 2/2010 | |
| WO | WO-2010/016940 A2 | 2/2010 | |
| WO | WO-2010/029159 A1 | 3/2010 | |
| WO | WO-2010/070251 A1 | 6/2010 | |
| WO | WO-2010/070252 A1 | 6/2010 | |
| WO | WO-2010/070253 A1 | 6/2010 | |
| WO | WO-2010/070255 A1 | 6/2010 | |
| WO | WO-2010070253 A1 * | 6/2010 | ............... A61P 1/16 |
| WO | WO-2010/080606 A1 | 7/2010 | |
| WO | WO-2010/080609 A1 | 7/2010 | |
| WO | WO-2010/096052 A1 | 8/2010 | |
| WO | WO-2010/148089 A1 | 12/2010 | |
| WO | WO-2011/006497 A1 | 1/2011 | |
| WO | WO-2011/080103 A1 | 7/2011 | |
| WO | WO-2011/084808 A2 | 7/2011 | |
| WO | WO-2011/088837 A1 | 7/2011 | |
| WO | WO-2011/094337 A1 | 8/2011 | |
| WO | WO-2011/117416 A1 | 9/2011 | |
| WO | WO-2011/117417 A1 | 9/2011 | |
| WO | WO-2011/119657 A1 | 9/2011 | |
| WO | WO-2011/134471 A1 | 11/2011 | |
| WO | WO-2011/160630 A2 | 12/2011 | |
| WO | WO-2011/160633 A1 | 12/2011 | |
| WO | WO-2012/062803 A1 | 5/2012 | |
| WO | WO-2012/062804 A1 | 5/2012 | |
| WO | WO-2012/098462 A1 | 7/2012 | |
| WO | WO-2012/130866 A1 | 10/2012 | |
| WO | WO-2012/140117 A1 | 10/2012 | |
| WO | WO-2012/150503 A1 | 11/2012 | |
| WO | WO-2012/153196 A2 | 11/2012 | |
| WO | WO-2012/167744 A1 | 12/2012 | |
| WO | WO-2013/041678 A1 | 3/2013 | |
| WO | WO-2013/092703 A2 | 6/2013 | |
| WO | WO-2013/164483 A1 | 11/2013 | |
| WO | WO-2014/016300 A1 | 1/2014 | |
| WO | WO-2014/041195 A1 | 3/2014 | |
| WO | WO-2015/067715 A2 | 5/2015 | |
| WO | WO-2015/124612 A1 | 8/2015 | |
| WO | WO-2016/166289 A1 | 10/2016 | |

OTHER PUBLICATIONS

Deacon et al., Diabetologia (1998) 41:271-278 (Year: 1998).*
Fernando et al., Abstract for ACS Spring 2022 Conference, 1 page (Year: 2022).*
Ng and Henikoff, Annu. Rev. Genomics Hum. Genet. 2006. 7:61-80 (Year: 2006).*
U.S. Appl. No. 14/843,047, filed May 5, 2016, Zealand Pharma A/S.
U.S. Appl. No. 60/132,018, Prickett et al.
U.S. Appl. No. 61/784,294, Tolborg et al.
Abbrecht et al., "Erythrocyte life-span in mice acclimatized to different degrees of hypoxia," J Appl Physiol. 32(4):443-445 (1972).
Action Closing Prosecution in Inter Partes Reexam 95/000,276, dated Mar. 17, 2011 (25 pages).
Adelhorst et al., "Structure-activity studies of glucagon-like peptide-1," J Biol Chem 269(9):6275-6278 (1994).
Ali et al., "Cardiomyocyte glucagon receptor signaling modulates outcomes in mice with experimental myocardial infarction," Mol Metab. 4(2):132-143 (2015).
Ally et al., "Rapid determination of creatine, phosphocreatine, purine bases and nucleotides (ATP, ADP, AMP, GTP, GDP) in heart biopsies by gradient ion-pair reversed-phase liquid chromatography," J Chromatogr. 575(1):19-27 (1992).
Altschul et al., "Local alignment statistics," Methods Enzymol. 266:460-480 (1996).
Arnold, "Heart failure," <http://www.merckmanuals.com/home/heart_and_blood_vessel_disorders/heart_failure/heart_failure.html?qt=congestive_heart_failure&alt=sh>, retrieved on Feb. 8, 2015 (12 pages).
Authier et al., "Endosomal proteolysis of glucagon at neutral pH generates the bioactive degradation product miniglucagon-(19-29)," Endocrinology. 144(12):5353-5364 (2003).
Bailey et al., "Glucagon-like peptide-1 and the entero-insular axis in obese hyperglycaemic (ob/ob) mice," Life Sci. 40(6):521-525 (1987).
Ban et al., "Cardioprotective and vasodilatory actions of glucagon-like peptide 1 receptor are mediated through both glucagon-like peptide 1 receptor-dependent and -independent pathways," Circulation. 117(18):2340-2350 (2008).
Bedford et al., "Amino acid structure and 'difficult sequences' in solid phase peptide synthesis," Int J Peptide Protein Res. 40(3-4):300-7 (1992).
Behme et al., "Glucagon-like peptide 1 improved glycemic control in Type 1 diabetes," BMC Endocr Disord. 3(1):3 (2003) (9 pages).
Bell, "Heart failure: the frequent, forgotten, and often fatal complication of diabetes," Diabetes Care. 26(8):2433-41 (2003).
Blache et al., "Endopeptidase from rat liver membranes, which generates miniglucagon from glucagon," J Biol Chem. 268(29):21748-21753 (1993).
Bork, "Powers and pitfalls in sequence analysis: the 70% hurdle," Genome Research 10, 398-400, 2000.
Bowie et al., "Deciphering the message in protein sequences: tolerance to amino acid substitutions," Science. 247(4948):1306-10 (1990).
Burcelin et al., "Long-lasting antidiabetic effect of a dipeptidyl peptidase IV-resistant analog of glucagon-like peptide-1," Metabolism. 48(2):252-258 (1999).
Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111, 2129-38, 1990.
Buse et al., "The effect of epinephrine, glucagon, and the nutritional state on the oxidation of branched chain amino acids and pyruvate by isolated hearts and diaphragms of the rat," J Biol Chem. 248(2):697-706 (1973).
Buse, "Progressive use of medical therapies in type 2 diabetes," Diabetes Spectrum. 13(4):211-20 (2000).
Byrne et al., "Inhibitory effects of hyperglycaemia on fed jejunal motility: potential role of hyperinsulinaemia," Eur J Clin Invest. 28(1):72-78 (1998).
Carpenter et al., "Rational design of stable lyophilized protein formulations: some practical advice," Pharm Res. 14(8):969-75 (1997).
Cavanaugh et al., "Isolation and structural characterization of proglucagon-derived peptides, pancreatic polypeptide, and somatostatin from the urodele Amphiuma tridactylum," Gen Comp Endocrinol. 101(1):12-20 (1996).
Chabenne et al., "Optimization of the native glucagon sequence for medicinal purposes," J Diabetes Sci Technol. 4(6):1322-31 (2010).
Chan et al., "Suppression of weight gain by glucagon in obese Zucker rats," Exp Mol Path. 40(3):320-327 (1984).

(56) References Cited

OTHER PUBLICATIONS

Chen et al., "Evidence that the diabetes gene encodes the leptin receptor: identification of a mutation in the leptin receptor gene in db/db mice," Cell. 84(3):491-5 (1996).
Chen et al., "Tissue-specific expression of unique mRNAs that encode proglucagon-derived peptides or exendin 4 in the lizard," J Biol Chem. 272(7):4108-15 (1997).
Cleland et al., "The development of stable protein formulations: a close look at protein aggregation, deamidation, and oxidation," Crit Rev Ther Drug Carrier Syst. 10(4):307-77 (1993).
Cohen et al., "Oxyntomodulin suppresses appetite and reduces food intake in humans," J Clin Endocrinol Metab. 88(10):4696-4701 (2003).
Coleman, "Effects of parabiosis of obese with diabetes and normal mice," Diabetologia. 9(4):294-8 (1973).
Communication from the European Patent Office for European Patent Application No. 08875673.9, dated Jul. 4, 2012 (6 pages).
D'Alessio et al., "Glucagon-like peptide 1 enhances glucose tolerance both by stimulation of insulin release and by increasing insulin-independent glucose disposal," J Clin Invest. 93(5):2263-66 (1994).
Dakin et al., "Oxyntomodulin inhibits food intake in the rat," Endocrinology. 142(10):4244-4250 (2001).
Dakin et al., "Peripheral oxyntomodulin reduces food intake and body weight gain in rats," Endocrinology. 145(6):2687-2695 (2004).
Day et al., "A new glucagon and GLP-1 co-agonist eliminates obesity in rodents," Nat Chem Biol. 5(10):749-757 (2009).
De Boer et al., "The tac promoter: a functional hybrid derived from the trp and lac promoters," Proc Natl Acad Sci USA. 80(1):21-5 (1983).
Deacon et al., "Dipeptidyl peptidase IV inhibition potentiates the insulinotropic effect of glucagon-like peptide 1 in the anesthetized pig," Diabetes. 47(5):764-9 (1998).
Deacon et al., "Dipeptidyl peptidase IV resistant analogues of glucagon-like peptide-1 which have extended metabolic stability and improved biological activity," Diabetologia. 41(3):271-8 (1998).
Decision in Inter Partes Reexam for U.S. Appl. No. 95/000,276, dated Nov. 25, 2013 (29 pages).
Delgado et al., "The uses and properties of PEG-linked proteins," Crit Rev Ther Drug Carrier Syst. 9(3,4):249-304 (1992).
Diamant et al., "Diabetic cardiomyopathy in uncomplicated type 2 diabetes is associated with the metabolic syndrome and systemic inflammation," Diabetologia 48(8):1669-70 (2005).
Dickstein et al., "ESC Guidelines for the diagnosis and treatment of acute and chronic heart failure 2008: the Task Force for the diagnosis and treatment of acute and chronic heart failure 2008 of the European Society of Cardiology. Developed in collaboration with the Heart Failure Association of the ESC (HFA) and endorsed by the European Society of Intensive Care Medicine (ESICM)," Eur Heart J. 29(19):2388-442 (2008).
Druce et al., "Investigation of structure-activity relationships of Oxyntomodulin (Oxm) using Oxm analogs," Endocrinology. 150(4):1712-1721 (2009).
Drucker, "Glucagon-like peptides," Diabetes. 47(2):159-69 (1998).
Ebert et al., "Gastric inhibitory polypeptide," Clin Gastroenterol. 9(3):679-98 (1980).
Edvell et al., "Initiation of increased pancreatic islet growth in young normoglycemic mice (Umeå +/?)," Endocrinology. 140(2):778-83 (1999).
Ehrlich, "DNA cloning in Bacillus subtilis," Proc Natl Acad Sci USA. 75(3):1433-6 (1978).
EMEA Humalog Information: European Public Assessment Report (EPAR) and Scientific Discussions, 2006 (11 pages).
Eng et al., "Isolation and characterization of exendin-4, an exendin-3 analogue, from Heloderma suspectum venom. Further evidence for an exendin receptor on dispersed acini from guinea pig pancreas.," J Biol Chem. 267(11):7402-7405 (1992).
England et al., "Glucagon carboxyl-terminal derivatives: Preparation, purification and characterization," Biochemistry. 21(5):940-950 (1982).

English Translation of Notice of Reasons for Rejection from Office Action for Japanese Application No. 2015-523532, dated Apr. 24, 2018 (8 pages).
European Search Opinion and Extended European Search Report for European Patent Application No. 08016668.9, dated Jan. 27, 2009 (5 pages).
European Search Report for European Application No. 09002937, dated Mar. 15, 2010 (5 pages).
European Search Report for European Application No. 99610043, dated Jan. 18, 2000 (2 pages).
European Search Report from European Patent Application No. 07016032.0, completed Jan. 28, 2008 (8 pages).
Extended European Search Report for European Patent Application No. 11774431.8, dated Sep. 30, 2013 (11 pages).
Fang et al., "Diabetic cardiomyopathy: evidence, mechanisms, and therapeutic implications," Endocr Rev. 25(4):543-67 (2004).
Farah et al., "Studies on the pharmacology of glucagon," J Pharmacol Exp Ther. 129:49-55 (1960).
Finan et al., "Reappraisal of GIP Pharmacology for Metabolic Diseases," Trends Mol Med. 22(5):359-76 (2016).
Fineman et al., Abstract 343-OR: "AC2993 (Synthetic Exendin-4) added to existing metformin (Met) and/or Sulfonylurea (SFU) treatment improved glycemic control in patients with type 2 diabetes (DM2) during 28 days of treatment," Diabetes. 51(Supplement 2):A85, Abstract Book, 62nd Scientific Sessions (2002) (3 pages).
First Examination Report for New Zealand Patent Application No. 702333, dated Jun. 2, 2016 (4 pages).
Francis et al., "PEGylation of cytokines and other therapeutic proteins and peptides: the importance of biological optimisation of coupling techniques," Int J Hematol. 68(1):1-18 (1998).
Frandsen et al., "Glucagon: structure-function relationships investigated by sequence deletions," Hoppe Seylers Z Physiol Chem. 362(6):665-677 (1981).
Gault et al., "Administration of an acylated GLP-1 and GIP preparation provides added beneficial glucose-lowering and insulinotropic actions over single incretins in mice with Type 2 diabetes and obesity," Clin Sci (Lond). 121(3):107-17 (2011).
Gelfanov et al., Discovery and structural optimization of high affinity co-agonists at the glucagon and GLP-1 receptors. Understanding Biology Using Peptides. Sylvie E. Blondelle, 763-764 (2005).
Goldstein et al., "Effects of chronic heart failure on the capacity of glucagon to enhance contractility and adenyl cyclase activity of human papillary muscles," Circulation. 44(4):638-648 (1971).
Gombotz et al. "Biodegradable polymers for protein and peptide drug delivery," Bioconjug Chem. 6(4):332-351 (1995).
Green et al., "Structurally modified analogues of glucagon-like peptide-1 (GLP-1) and glucose-dependent insulinotropic polypeptide (GIP) as future antidiabetic agents," Curr Pharm Des. 10(29):3651-62 (2004).
Greig et al., "Once daily injection of exendin-4 to diabetic mice achieves long-term beneficial effects on blood glucose concentrations," Diabetologia. 42(1):45-50 (1999).
Grieve et al., "Emerging cardiovascular actions of the incretin hormone glucagon-like peptide-1: Potential therapeutic benefits beyond glycaemic control?," Br J Pharmacol. 157(8):1340-51 (2009).
Gunn et al., "Central glucagon-like peptide-I in the control of feeding," Biochem Soc Trans. 24(2):581-4 (1996).
Guo et al., "3'-end-forming signals of yeast mRNA," Mol Cell Biol. 15(11):5983-90 (1995).
Gutniak et al., "Antidiabetogenic effect of glucagon-like peptide-1 (7-36)amide in normal subjects and patients with diabetes mellitus," N Engl J Med. 326(20):1316-22 (1992).
Göke et al., "Distribution of GLP-1 binding sites in the rat brain: Evidence that exendin-4 is a ligand of brain GLP-1 binding sites," Eur J Neurosci. 7(11):2294-2300 (1995).
Göke et al., "Exendin-4 is a high potency agonist and truncated exendin-(9-39)-amide an antagonist at the glucagon-like peptide 1-(7-36)-amide receptor of insulin-secreting beta-cells," J Biol Chem. 268(26):19650-19655 (1993).

(56) References Cited

OTHER PUBLICATIONS

Haffner et al., "Intensive lifestyle intervention or metformin on inflammation and coagulation in participants with impaired glucose tolerance," Diabetes. 54(5):1566-72 (2005).
Hamad et al., "Pharmacologic therapy of chronic heart failure," Am J Cardiovasc Drugs. 7(4):235-48 (2007).
Hansson, "Inflammation, atherosclerosis, and coronary artery disease," N Engl J Med. 352(16):1685-95 (2005).
Harikae, "The effects of a behavioral program in the obese NIDDM patients—observations on daily activity, degree of obesity and blood sugar control," Bulletin of the School of Nursing, Yamaguchi Prefectural University 2:1-13/E (1998) (Abstract in English).
Heinrich et al., "Pre-proglucagon messenger ribonucleic acid: nucleotide and encoded amino acid sequences of the rat pancreatic complementary deoxyribonucleic acid," Endocrinology. 115(6):2176-81 (1984).
Hjorth et al., "Glucagon and glucagon-like peptide 1: Selective receptor recognition via distinct peptide epitopes," J Biol Chem. 269(48):30121-30124 (1994).
Holst, "Enteroglucagon," Annu Rev Physiol. 59:257-71 (1997).
Holst, "Glucagon-like peptide-1, a gastrointestinal hormone with a pharmaceutical potential," Curr Med Chem. 6(11):1005-17 (1999).
Holst, "The physiology of glucagon-like peptide 1," Physiol Rev. 87(4): 1409-39 (2007).
Hostrup et al., Modification of Peptides and Proteins. Delivery Technologies for Biopharmaceuticals: Peptides, Proteins, Nucleic Acids and Vaccines. Jorgensen, Nielsen, 171-91 (2009).
Hruby et al., "The design and biological activities of glucagon agonists and antagonists, and their use in examining the mechanisms of glucose action," Curr Med Chem—Imm, Endoc Metab Agents. 1(3):199-215 (2001).
Hudecz et al., "Synthesis, conformation, biodistribution, and in vitro cytotoxicity of daunomycin-branched polypeptide conjugates," Bioconjug Chem. 3(1):49-57 (1992).
Hui et al., "The short half-life of glucagon-like peptide-1 in plasma does not reflect its long-lasting beneficial effects," Eur J Endocrinol. 146(6):863-9 (2002).
Ingwall et al., "Is the failing heart energy starved?: On using chemical energy to support cardiac function," Circ Res. 95(2):135-45 (2004).
International Preliminary Examination Report for International Application No. PCT/DK03/00463, dated Sep. 20, 2004 (5 pages).
International Preliminary Report on Patentability for PCT/EP2013/069286, completed Jan. 19, 2015 (40 pages).
International Preliminary Report on Patentability for PCT/GB2008/002041, dated Dec. 17, 2009 (7 pages).
International Search Report and Written Opinion for International Application No. PCT/IB2012/001090, dated Jan. 25, 2013 (15 pages).
International Search Report and Written Opinion for International Patent Application No. PCT/EP2012/071766, dated Feb. 15, 2013 (9 pages).
International Search Report and Written Opinion for PCT/EP2013/059319, dated Sep. 12, 2013 (12 pages).
International Search Report and Written Opinion for PCT/EP2013/065519, dated Dec. 6, 2013 (11 pages).
International Search Report and Written Opinion for PCT/EP2013/069286, dated Dec. 18, 2013 (16 pages).
International Search Report and Written Opinion for PCT/EP2016/058359, dated Jul. 15, 2016 (13 pages).
International Search Report and Written Opinion for PCT/GB2008/004121, dated Jun. 30, 2009 (25 pages).
International Search Report and Written Opinion for PCT/GB2008/004130, dated Mar. 25, 2009 (17 pages).
International Search Report and Written Opinion for PCT/GB2008/004132, dated Jun. 10, 2009 (16 pages).
International Search Report for International Application No. PCT/DK00/00393, dated Nov. 8, 2000 (3 pages).
International Search Report for International Application No. PCT/DK03/00463, dated Oct. 22, 2003 (7 pages).
International Search Report for International Application No. PCT/DK2010/000099, dated Dec. 2, 2010 (2 pages).
International Search Report for International Application No. PCT/DK2011/000067, dated Dec. 9, 2011 (4 pages).
International Search Report for International Application No. PCT/DK2011/050133, dated Oct. 6, 2011 (5 pages).
International Search Report for International Application No. PCT/IB2012/000134, dated Jun. 25, 2012 (3 pages).
International Search Report for International Application No. PCT/DK2011/050018, dated May 30, 2011 (6 pages).
International Search Report for PCT/DK2011/000072, dated Dec. 6, 2011 (3 pages).
International Search Report for PCT/GB2008/002041, dated Sep. 9, 2008 (3 pages).
International Search Report for PCT/GB2008/004157, dated Jun. 4, 2009 (21 pages).
Irwin et al., "Antidiabetic potential of two novel fatty acid derivatised, N-terminally modified analogues of glucose-dependent insulinotropic polypeptide (GIP): N-AcGIP(LysPAL16) and N-AcGIP(LysPAL37)," Biol Chem. 386(7):679-87 (2005).
Irwin et al., "GIP(Lys16PAL) and GIP(Lys37PAL): novel long-acting acylated analogues of glucose-dependent insulinotropic polypeptide with improved antidiabetic potential," J Med Chem. 49(3):1047-54 (2006).
Jaya et al., "Mechanism of hypocholesterolemic action of glucagon," J Biosci. 12(2):111-4 (1987).
Jessup et al., "2009 focused update: ACCF/AHA Guidelines for the Diagnosis and Management of Heart Failure in Adults: a report of the American College of Cardiology Foundation/American Heart Association Task Force on Practice Guidelines: developed in collaboration with the International Society for Heart and Lung Transplantation.," Circulation. 119(14):1977-2016 (2009).
Joshi et al., "The estimation of glutaminyl deamidation and aspartyl cleavage rates in glucagon," Int J Pharm. 273(1-2):213-219 (2004).
Juntti-Berggren et al., "The antidiabetogenic effect of GLP-1 is maintained during a 7-day treatment period and improves diabetic dyslipoproteinemia in NIDDM patients," Diabetes Care. 19(11):1200-6 (1996).
Kallenbach et al., Role of the peptide bond in protein structure and folding. The Amide Linkage: Selected Structural Aspects in Chemistry, Biochemistry, and Materials Science. Greenberg, Breneman, Liebman, 599-625 (2000).
Kawashima et al., "Case of pancreatic diabetes with improvement in carbohydrate and lipid metabolism brought about by injections of a small quantity of glucagon," The Journal of the Japanese Society of Internal Medicine. 88(2):336-8 (1999) (English Abstract Included).
Knudsen et al., "Potent derivatives of glucagon-like peptide-1 with pharmacokinetic properties suitable for once daily administration," J Med Chem. 43(9):1664-1669 (2000).
Korc, "Islet growth factors: curing diabetes and preventing chronic pancreatitis?," J Clin Invest. 92(3):1113-4 (1993).
Krchnák et al., "Aggregation of resin-bound peptides during solid-phase peptide synthesis. Prediction of difficult sequences," Int J Pept Protein Res. 42(5):450-4 (1993).
Larsen et al., "Sequence-assisted peptide synthesis (SAPS)," J Peptide Res. 52(6):470-6 (1998).
Lazar et al., "Transforming growth factor alpha: mutation of aspartic acid 47 and leucine 48 results in different biological activities," Mol. Cell. Biol. 8, 1247-52, 1988.
Lefébvre, "The intriguing diversity of the glucagon gene products," Curr Diab Rep. 2(3):201-2 (2002).
Leiter et al., "Influence of dietary carbohydrate on the induction of diabetes in C57BL/KsJ-db/db diabetes mice," J Nutr. 113(1):184-95 (1983).
Levey et al., "Activation of adenyl cyclase by glucagon in cat and human heart," Circ Res. 24(2):151-6 (1969).
Lopaschuk et al., "Measurements of fatty acid and carbohydrate metabolism in the isolated working rat heart," Mol Cell Biochem. 172(1-2):137-47 (1997).
Loyter et al., "Mechanisms of DNA uptake by mammalian cells: fate of exogenously added DNA monitored by the use of fluorescent dyes," Proc Natl Acad Sci USA. 79(2):422-6 (1982).

(56) References Cited

OTHER PUBLICATIONS

Lvoff et al., "Glucagon in heart failure and in cardiogenic shock. Experience in 50 patients," Circulation. 45(3):534-42 (1972).
López-Delgado et al., "Effects of glucagon-like peptide 1 on the kinetics of glycogen synthase a in hepatocytes from normal and diabetic rats," Endocrinology. 139(6):2811-17 (1998).
Madsen et al., "Structure-activity and protraction relationship of long-acting glucagon-like peptide-1 derivatives: importance of fatty acid length, polarity, and bulkiness," J Med Chem. 50(24):6126-32 (2007).
Malde et al., "Understanding interactions of gastric inhibitory polypeptide (GIP) with its G-protein coupled receptor through NMR and molecular modeling," J Pept Sci. 13(5):287-300 (2007).
Manhart et al., "Structure-function analysis of a series of novel GIP analogues containing different helical length linkers," Biochemistry. 42(10):3081-8 (2003).
Manning et al., "Stability of protein pharmaceuticals," Pharm Res. 6(11):903-18 (1989).
Matsumoto et al., "Plasma Incretin Levels and Dipeptidyl Peptidase-4 Activity in Patients with Obstructive Sleep Apnea," Ann Am Thorac Soc. 13(8):1378-87 (2016).
Matsuyama, "Glucagon and diabetes," Shijonawate Gakuen Bulletin of Faculty of Rehabilitation. 7:1-12 (2011) (English Abstract Included).
Matthes et al., "Simultaneous rapid chemical synthesis of over one hundred oligonucleotides on a microscale," EMBO J. 3(4):801-5 (1984).
Mayer et al., "Effect of glucagon on cyclic 3',5'-AMP, phosphorylase activity and contractility of heart muscle of the rat," Circ Res. 26(2):225-33 (1970).
McKee et al., "Receptor binding and adenylate cyclase activities of glucagon analogues modified in the N-terminal region," Biochemistry. 25(7):1650-1656 (1986).
Mehta, "Diabetic cardiomyopathy: insights into pathogenesis, diagnostic challenges, and therapeutic options," Intl J Pharm Sci Res. 3(10):3565-3576 (2012).
Meurer et al., "Properties of native and in vitro glycosylated forms of the glucagon-like peptide-1 receptor antagonist exendin (9-39)," Metabolism. 48(6):716-24 (1999).
Meyer et al., Effects of conformation on the Chemical Stability of Pharmaceutically Relevant Polypeptides. *Rational design of stable protein formulations*. Carpenter and Manning, 85-6 (2002).
Mojsov, "Structural requirements for biological activity of glucagon-like peptide-I," Int J Pept Protein Res. 40(3-4):333-43 (1992).
Nauck et al., "Glucagon-like peptide 1 and its potential in the treatment of non-insulin-dependent diabetes mellitus," Horm Metab Res. 29(9):411-6 (1997).
Navarro et al., "Colocalization of glucagon-like peptide-1 (GLP-1) receptors, glucose transporter GLUT-2, and glucokinase mRNAs in rat hypothalamic cells: evidence for a role of GLP-1 receptor agonists as an inhibitory signal for food and water intake," J Neurochem 67(5):1982-91 (1996).
NCBI Blast for Accession No. 721913A, retrieved on Dec. 15, 2009 (1 page).
Neubauer et al., "Myocardial phosphocreatine-to-ATP ratio is a predictor of mortality in patients with dilated cardiomyopathy," Circulation. 96(7):2190-6 (1997) (9 pages).
Neumann et al., "Gene transfer into mouse lyoma cells by electroporation in high electric fields," EMBO J. 1(7):841-5 (1982).
Nikolaidis et al., "Active metabolite of GLP-1 mediates myocardial glucose uptake and improves left ventricular performance in conscious dogs with dilated cardiomyopathy," Am J Physiol Heart Circ Physiol. 289(6):H2401-8 (2005).
Nikolaidis et al., "Recombinant glucagon-like peptide-1 increases myocardial glucose uptake and improves left ventricular performance in conscious dogs with pacing-induced dilated cardiomyopathy," Circulation. 110(8):955-61 (2004).
Notice of Allowance and Allowed Claims for U.S. Appl. No. 13/383,783, dated Jun. 22, 2015 (5 pages).
Notice of Allowance, previously Allowed Claims and Amendment after Allowance for U.S. Appl. No. 13/704,299, dated Jun. 26, 2015 (15 pages).
Notice of Allowance, previously Allowed Claims and Amendment after Allowance for U.S. Appl. No. 14/029,529, dated Jun. 29, 2015 (14 pages).
Notice of Opposition to a European Patent for European Patent No. 1525219 on behalf of Novo Nordisk A/S, dated Feb. 25, 2010 (24 pages).
Office Action for Colombian Application No. 16089238, dated Sep. 13, 2017 (18 pages).
Orskov, "Glucagon-like peptide-1, a new hormone of the entero-insular axis," Diabetologia. 35(8):701-11 (1992).
Overgaard et al., "Inotropes and vasopressors: review of physiology and clinical use in cardiovascular disease," Circulation. 118(10):1047-56 (2008).
Owens et al., "Insulins today and beyond," Lancet. 358(9283):739-46 (2001).
Pan et al., "Design of a long acting peptide functioning as both a glucagon-like peptide-1 receptor agonist and a glucagon receptor antagonist," J Biol Chem. 281(18):12506-12515 (2006).
Parkes et al., "Insulinotropic actions of exendin-4 and glucagon-like peptide-1 in vivo and in vitro," Metabolism. 50(5):583-9 (2001).
Parlevliet et al., "CNTO736, a novel glucagon-like peptide-1 receptor agonist, ameliorates insulin resistance and inhibits very low-density lipoprotein production in high-fat-fed mice." J Pharmacol Exp Ther. 328(1):240-8 (2009).
Parlevliet et al., "Oxyntomodulin ameliorates glucose intolerance in mice fed a high-fat diet," Am J Physiol Endocrinol Metab. 294(1):E142-E147 (2008).
Partial European Search Report for European Application No. 03005786, dated Oct. 23, 2003 (6 pages).
Partial European Search Report for European Application No. 99610043, dated Jan. 18, 2000 (4 pages).
Pederson et al., "Improved glucose tolerance in Zucker fatty rats by oral administration of the dipeptidyl peptidase IV inhibitor isoleucine thiazolidide," Diabetes. 47(8):1253-8 (1998).
Perfetti et al., "Glucagon-like peptide-1: a major regulator of pancreatic beta-cell function," Eur J Endocrinol. 143(6): 717-25 (2000).
Periasamy et al., "Molecular basis of diastolic dysfunction," available in PMC Jul. 6, 2009, published in final edited form as: Heart Fail Clin. 4(1):13-21 (2008) (13 pages).
Petersen et al., "ZP10—A new GLP-1 agonist that prevents diabetes progression and increases insulin mRNA expression in db/db mice," 38th Annual Meeting of the European Association for the Study of Diabetes (EASD). Budapest, Hungary, Sep. 1-5, 2002, *Diabetologia* 45 (Suppl. 1):A147, Abstract No. 447 (2002) (2 pages).
Pocai et al., "Glucagon-like peptide 1/glucagon receptor dual agonism reverses obesity in mice," Diabetes. 58(10):2258-66 (2009).
Pocai, "Glucagon signaling in the heart: activation or inhibition?," Mol Metab. 4(2):81-2 (2015).
Pohl et al., "Molecular cloning of the helodermin and exendin-4 cDNAs in the lizard. Relationship to vasoactive intestinal polypeptide/pituitary adenylate cyclase activating polypeptide and glucagon-like peptide 1 and evidence against the existence of mammalian homologues," J Biol Chem. 273(16):9778-84 (1998).
Poon et al., "Exenatide improves glycemic control and reduces body weight in subjects with type 2 diabetes: a dose-ranging study," Diabetes Technol Ther. 7(3):467-77 (2005).
Pratesi et al., "Poly-L-aspartic acid as a carrier for doxorubicin: a comparative in vivo study of free and polymer-bound drug," Br J Cancer. 52(6):841-848 (1985).
Pridal et al., "Absorption of glucagon-like peptide-1 can be protracted by zinc or protamine," Int J Pharm. 136(1-2):53-9 (1996).
Protest of U.S. Appl. No. 12/664,534 Pursuant 37 CFR 1.291, dated Jan. 13, 2010 (14 pages).
Raufman et al., "Exendin-3, a novel peptide from *Heloderma horridum* venom, interacts with vasoactive intestinal peptide receptors and a newly described receptor on dispersed acini from guinea pig pancreas. Description of exendin-3(9-39) amide, a specific exendin receptor antagonist," J Biol Chem. 266(5):2897-902 (1991).

(56) References Cited

OTHER PUBLICATIONS

Raufman et al., "Truncated glucagon-like peptide-1 interacts with exendin receptors on dispersed acini from guinea pig pancreas. Identification of a mammalian analogue of the reptilian peptide exendin-4," J Biol Chem. 267(30):21432-7 (1992).
Raufman, "Bioactive peptides from lizard venoms," Regul Pept. 61(1):1-18 (1996).
Ritzel et al., "A synthetic glucagon-like peptide-1 analog with improved plasma stability," J Endocrinol. 159(1):93-102 (1998).
Roach et al., "Improved postprandial glycemic control during treatment with humalog Mix25, a novel protamine-based insulin lispro formulation. Humalog Mix25 Study Group," Diabetes Care. 22(8):1258-61 (1999).
Robberecht et al., "Comparative efficacy of seven synthetic glucagon analogs, modified in position 1, 2, and/or 12, on liver and heart adenylate cyclase from rat," Peptides. 7(Suppl 1):109-12 (1986).
Rolin et al., "The long-acting GLP-1 derivative NN2211 ameliorates glycemia and increases beta-cell mass in diabetic mice," Am J Physiol Endocrinol Metab. 283(4):E745-52 (2002).
Rooman et al., "Gastrin stimulates beta-cell neogenesis and increases islet mass from transdifferentiated but not from normal exocrine pancreas tissue," Diabetes. 51(3):686-90 (2002).
Rose et al., "Insulin proteinase liberates from glucagon a fragment known to have enhanced activity against Ca2+ + Mg2+-dependent ATPase," Biochem J. 256(3):847-51 (1988).
Runge et al., "Differential structural properties of GLP-1 and exendin-4 determine their relative affinity for the GLP-1 receptor N-terminal extracellular domain," Biochemistry. 46(19):5830-40 (2007).
Saraceni et al., "Effects of glucagon-like peptide-1 and long-acting analogues on cardiovascular and metabolic function," Drugs R D. 8(3):145-53 (2007).
Sowden et al., "Oxyntomodulin increases intrinsic heart rate in mice independent of the glucagon-like peptide-1 receptor," Am J Physiol Regul Integr Comp Physiol. 292(2): R962-70 (2007).
Stoffers et al., "Insulinotropic glucagon-like peptide 1 agonists stimulate expression of homeodomain protein IDX-1 and increase islet size in mouse pancreas," Diabetes. 49(5):741-8 (2000).
Sturm et al., "Structure-function studies on positions 17, 18, and 21 replacement analogues of glucagon: the importance of charged residues and salt bridges in glucagon biological activity," J Med Chem. 41(15): 2693-700 (1998) (8 pages).
Suarez-Pinzon et al., "Combination therapy with epidermal growth factor and gastrin increases beta-cell mass and reverses hyperglycemia in diabetic NOD mice," Diabetes. 54(9):2596-601 (2005).
Suarez-Pinzon et al., "Combination therapy with glucagon-like peptide-1 and gastrin restores normoglycemia in diabetic NOD mice," Diabetes. 57(12):3281-8 (2008).
Tang-Christensen et al., "Central administration of GLP-1-(7-36) amide inhibits food and water intake in rats," Am J. Physiol. 271(4 Pt 2):R848-56 (1996).
Thorkildsen et al., "The exendin analogue ZP10 increases insulin mRNA expression in db/db mice," Nedergaard Symposium, Odense, Denmark, Jan. 24, 2002 (Poster presentation) (1 page).
Thorkildsen et al., "ZP10—A New GLP-1 agonist that increases insulin mRNA expression," Nedergaard Symposium, Odense, Denmark, Jan. 24, 2002 (abstract only) (1 page).
Thorkildsen et al., "ZP10—A new GLP-1 agonist that prevents diabetes progression and increases insulin mRNA expression in db/db mice," 38th Annual Meeting of the European Associate for the Study of Diabetes (EASD), Budapest, Hungary, Sep. 1-5, 2002, Poster presentation (1 page).
Tomita et al., "Pancreatic islets of obese hyperglycemic mice (ob/ob)," Pancreas. 7(3):367-375 (1992).
Tourrel et al., "Persistent improvement of type 2 diabetes in the Goto-Kakizaki Rat model by expansion of the beta-cell mass during the prediabetic period with glucagon-like peptide-1 or exendin-4," Diabetes. 51(5):1443-52 (2002).

Tsukada et al., "An anti-alpha-fetoprotein antibody-daunorubicin conjugate with a novel poly-L-glutamic acid derivative as intermediate drug carrier," J Natl Cancer Inst. 73(3):721-729 (1984).
Turton et al., "A role for glucagon-like peptide-1 in the central regulation of feeding," Nature 379(6560):69-72 (1996).
U.S. Appl. No. 14/095,667, filed Dec. 3, 2013 (99 pages).
U.S. Appl. No. 14/116,268, filed Nov. 7, 2013 (164 pages).
U.S. Appl. No. 15/852,458, filed Dec. 22, 2017 (57 pages).
U.S. Appl. No. 60/132,018, filed Apr. 30, 1999 (101 pages).
Uesaka et al., "Glucagon-like peptide isolated from the eel intestine: Effects on atrial beating," J Exp Bio. 204(Pt 17):3019-26 (2001).
Underwood et al., "Crystal structure of glucagon-like peptide-1 in complex with the extracellular domain of the glucagon-like peptide-1 receptor," J Biol Chem. 285(1):723-30 (2010).
Unson et al., "Glucagon antagonists: contribution to binding and activity of the amino-terminal sequence 1-5, position 12, and the putative alpha-helical segment 19-27," J Biol Chem. 264(2):789-794 (1989).
Unson et al., "Identification of an essential serine residue in glucagon: implication for an active site triad," Proc Natl Acad Sci USA. 91(2):454-458 (1994).
Unson et al., "Positively charged residues at positions 12, 17, and 18 of glucagon ensure maximum biological potency," J Biol Chem. 273(17):10308-10312 (1998).
Uttenthal et al., "Molecular forms of glucagon-like peptide-1 in human pancreas and glucagonomas," J Clin Endocrinol Metabol. 61(3):472-479 (1985).
Villa-Komaroff et al., "A bacterial clone synthesizing proinsulin," Proc Natl Acad Sci USA. 75(8):3727-31 (1978).
Wang et al., "Glucagon-like peptide-1 treatment delays the onset of diabetes in 8 week-old db/db mice," Diabetologia. 45(9):1263-73 (2002).
Warnica, "Acute coronary syndromes (Heart Attack; Myocardial Infarction; Unstable Angina)," <http://www.merckmanuals.com/home/heart_and_blood_vessel_disorders/coronary_artery_disease/acute_coronary_syndromes_heart_attack_myocardial_infarction_unstable_angina.html?qt=congestive_heart_failure&alt=sh>, retrieved on Feb. 8, 2015 (8 pages).
Wermuth et al., "Glossary of terms used in medicinal chemistry," Pure & Appl Chem. 70(5):1129-43 (1998).
Wettergren et al., "Truncated GLP-1 (proglucagon 78-107-amide) inhibits gastric and pancreatic functions in man," Dig Dis Sci. 38(4):665-73 (1993).
White, "A review of potential cardiovascular uses of intravenous glucagon administration," J Clin Pharmacol. 39(5):442-7 (1999).
Wiberg et al., "Replication and expression in mammalian cells of transfected DNA; description of an improved erythrocyte ghost fusion technique," Nucleic Acids Res. 11(21):7287-7302 (1983).
Written Opinion for PCT/DK2011/000072, dated Dec. 6, 2011 (6 pages).
Written Opinion for Singapore Application No. 201209089-0, dated Nov. 8, 2013 (10 pages).
Written Opinion of the International Searching Authority for PCT/GB2008/002041, dated Sep. 9, 2008 (6 pages).
Xu et al., "Exendin-4 stimulates both beta-cell replication and neogenesis, resulting in increased beta-cell mass and improved glucose tolerance in diabetic rats," Diabetes. 48(12):2270-6 (1999).
Yabe et al., "Quantitative measurements of cardiac phosphorus metabolites in coronary artery disease by 31P magnetic resonance spectroscopy," Circulation. 92(1):15-23 (1995) (14 pages).
Yasgur, "Premature ventricle contractions in heart failure: a closer examination," http://www.thecardiologyadvisor.com/heart-failure/premature-ventricle-contractions-in-heart-failure/article/515445/, retrieved Sep. 10, 2017 (3 pages).
Young et al., "Glucose-lowering and insulin-sensitizing actions of exendin-4: studies in obese diabetic (ob/ob, db/db) mice, diabetic fatty Zucker rats, and diabetic rhesus monkeys (*Macaca mulatta*)," Diabetes. 48(5):1026-34 (1999).
Young et al., "Physiological and genetic factors affecting transformation of Bacillus subtilis," J Bacteriol. 81:823-9 (1961).
Zalipsky, "Functionalized poly(ethylene glycol) for preparation of biologically relevant conjugates," Bioconjug Chem. 6(2):150-165 (1995).

(56) References Cited

OTHER PUBLICATIONS

Zander et al., "Additive glucose-lowering effects of glucagon-like peptide-1 and metformin in type 2 diabetes," Diabetes Care. 24(4):720-5 (2001).

Zhao et al., "Direct effects of glucagon-like peptide-1 on myocardial contractility and glucose uptake in normal and postischemic isolated rat hearts," J Pharmacol Exp Ther. 317(3):1106-13 (2006).

Zhou et al., "Glucagon-like peptide 1 and exendin-4 convert pancreatic AR42J cells into glucagon-and insulin-producing cells," Diabetes. 48(12):2358-66 (1999).

Zhu et al.,"The role of dipeptidyl peptidase IV in the cleavage of glucagon family peptides: in vivo metabolism of pituitary adenylate cyclase activating polypeptide-(1-38)," J Biol Chem. 278(25):22418-22423 (2003).

\* cited by examiner

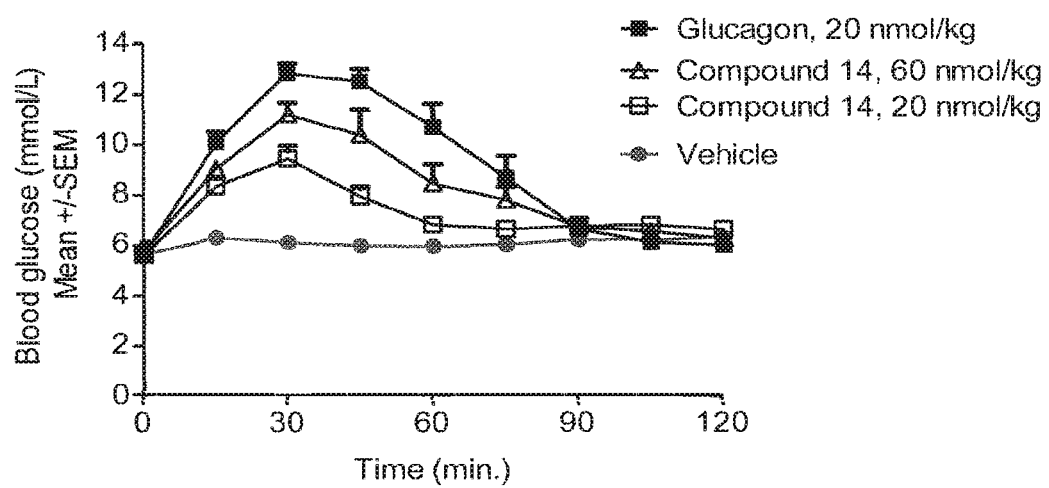

SEQUENCE LISTING

<160> NUMBER OF SEQ ID NOS: 44

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr 20          25

<210> SEQ ID NO 2
<211> LENGTH: 29
<212> TYPE: PRT
<213> ORGANISM: Artificial sequence
<220> FEATURE:
<223> OTHER INFORMATION: Synthetic compound

<400> SEQUENCE: 2

His Ser Gln Gly Thr Phe Thr Ser Asp Tyr Ser Lys Tyr Leu Asp Ser
1               5                   10                  15

Ala Arg Ala Glu Ser Phe Val Lys Trp Leu Glu Ser Thr
            20                  25

<210> SEQ ID NO 3
<211> LENGTH: 29
<212> TYPE: PRT
<213> ORGANISM: Artificial sequence
<220> FEATURE:
<223> OTHER INFORMATION: Synthetic compound

<400> SEQUENCE: 3

His Ser Gln Gly Thr Phe Thr Ser Asp Tyr Ser Lys Tyr Leu Asp Ser
1               5                   10                  15

Ala Arg Ala Glu Asp Phe Val Lys Trp Leu Glu Glu Thr
            20                  25

<210> SEQ ID NO 4
<211> LENGTH: 29
<212> TYPE: PRT
<213> ORGANISM: Artificial sequence
<220> FEATURE:
<223> OTHER INFORMATION: Synthetic compound

<400> SEQUENCE: 4

His Ser Gln Gly Thr Phe Thr Ser Asp Tyr Ser Lys Tyr Leu Asp Lys
1               5                   10                  15

Ala Arg Ala Glu Asp Phe Val Lys Trp Leu Glu Ser Thr
            20                  25

<210> SEQ ID NO 5
<211> LENGTH: 29
<212> TYPE: PRT
<213> ORGANISM: Artificial sequence
<220> FEATURE:
<223> OTHER INFORMATION: Synthetic compound

<400> SEQUENCE: 5

His Ser Gln Gly Thr Phe Thr Ser Asp Tyr Ser Lys Tyr Leu Asp Ser
1               5                   10                  15

Ala Arg Ala Glu Asp Phe Val Ala Trp Leu Glu Ser Thr
            20                  25

<210> SEQ ID NO 6
<211> LENGTH: 29
<212> TYPE: PRT
<213> ORGANISM: Artificial sequence
<220> FEATURE:
<223> OTHER INFORMATION: Synthetic compound

<400> SEQUENCE: 6

His Ser Gln Gly Thr Phe Thr Ser Asp Tyr Ser Lys Tyr Leu Asp Glu
1               5                   10                  15

Ala Arg Ala Lys Asp Phe Val Glu Trp Leu Glu Lys Thr
            20                  25

<210> SEQ ID NO 7
<211> LENGTH: 29
<212> TYPE: PRT
<213> ORGANISM: Artificial sequence
<220> FEATURE:
<223> OTHER INFORMATION: Synthetic compound

<400> SEQUENCE: 7

His Ser Gln Gly Thr Phe Thr Ser Asp Tyr Ser Lys Tyr Leu Asp Ser
1               5                   10                  15

Ala Arg Ala Glu Asp Phe Val Glu Trp Leu Glu Ser Thr
            20                  25

<210> SEQ ID NO 8
<211> LENGTH: 29
<212> TYPE: PRT
<213> ORGANISM: Artificial sequence
<220> FEATURE:
<223> OTHER INFORMATION: Synthetic compound

<400> SEQUENCE: 8

His Ser Gln Gly Thr Phe Thr Ser Asp Tyr Ser Arg Tyr Leu Glu Ser
1               5                   10                  15

Ala Arg Ala Glu Asp Phe Val Lys Trp Leu Glu Ser Thr
            20                  25

<210> SEQ ID NO 9
<211> LENGTH: 29
<212> TYPE: PRT
<213> ORGANISM: Artificial sequence
<220> FEATURE:
<223> OTHER INFORMATION: Synthetic compound

<400> SEQUENCE: 9

His Ser Gln Gly Thr Phe Thr Ser Asp Tyr Ser Lys Tyr Leu Glu Ser
1               5                   10                  15

Ala Arg Ala Glu Asp Phe Val Lys Trp Leu Glu Ser Thr
            20                  25

<210> SEQ ID NO 10
<211> LENGTH: 29
<212> TYPE: PRT
<213> ORGANISM: Artificial sequence
<220> FEATURE:
<223> OTHER INFORMATION: Synthetic compound

<400> SEQUENCE: 10

His Ser Gln Gly Thr Phe Thr Ser Asp Tyr Ser Lys Tyr Leu Asp Ser
1               5                   10                  15

Ala Arg Ala Glu Glu Phe Val Lys Trp Leu Glu Ser Thr
            20                  25

<210> SEQ ID NO 11
<211> LENGTH: 29
<212> TYPE: PRT
<213> ORGANISM: Artificial sequence
<220> FEATURE:
<223> OTHER INFORMATION: Synthetic compound

<400> SEQUENCE: 11

His Ser Gln Gly Thr Phe Thr Ser Asp Tyr Ser Lys Tyr Leu Asp Ser
1               5                   10                  15

```
Ala Arg Ala Glu Asp Phe Val Ser Trp Leu Glu Ser Thr
            20                  25
```

<210> SEQ ID NO 12
<211> LENGTH: 29
<212> TYPE: PRT
<213> ORGANISM: Artificial sequence
<220> FEATURE:
<223> OTHER INFORMATION: Synthetic compound

<400> SEQUENCE: 12

```
His Ser Gln Gly Thr Phe Thr Ser Asp Leu Ser Lys Tyr Leu Asp Ser
1               5                   10                  15

Ala Arg Ala Glu Asp Phe Val Lys Trp Leu Glu Ser Thr
            20                  25
```

<210> SEQ ID NO 13
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 13

```
His Ser Gln Gly Thr Phe Thr Ser Asp Tyr Ser Lys Tyr Leu Asp Xaa
1               5                   10                  15

Ala Arg Ala Glu Asp Phe Val Lys Trp Leu Glu Ser Thr
            20                  25
```

<210> SEQ ID NO 14
<211> LENGTH: 28
<212> TYPE: PRT
<213> ORGANISM: Artificial sequence
<220> FEATURE:
<223> OTHER INFORMATION: Synthetic compound

<400> SEQUENCE: 14

```
His Ser Gln Gly Thr Phe Thr Ser Asp Tyr Ser Lys Tyr Leu Asp Ser
1               5                   10                  15

Ala Arg Ala Glu Asp Phe Val Lys Trp Leu Glu Ser
            20                  25
```

<210> SEQ ID NO 15
<211> LENGTH: 29
<212> TYPE: PRT
<213> ORGANISM: Artificial sequence
<220> FEATURE:
<223> OTHER INFORMATION: Synthetic compound

<400> SEQUENCE: 15

```
His Ser Gln Gly Thr Phe Thr Ser Asp Tyr Ser Lys Tyr Leu Asp Glu
1               5                   10                  15

Ala Arg Ala Glu Asp Phe Val Lys Trp Leu Glu Ser Thr
            20                  25
```

<210> SEQ ID NO 16
<211> LENGTH: 29
<212> TYPE: PRT
<213> ORGANISM: Artificial sequence
<220> FEATURE:
<223> OTHER INFORMATION: Synthetic compound

```
<220> FEATURE:
<221> NAME/KEY: MISC_FEATURE
<222> LOCATION: (16)..(16)
<223> OTHER INFORMATION: Xaa is Aib

<400> SEQUENCE: 16

His Ser Gln Gly Thr Phe Thr Ser Asp Tyr Ser Lys Tyr Leu Asp Xaa
1               5                   10                  15

Ala Arg Ala Glu Ser Phe Val Lys Trp Leu Glu Ser Thr
            20                  25

<210> SEQ ID NO 17
<211> LENGTH: 29
<212> TYPE: PRT
<213> ORGANISM: Artificial sequence
<220> FEATURE:
<223> OTHER INFORMATION: Synthetic compound

<400> SEQUENCE: 17

His Ser Gln Gly Thr Phe Thr Ser Asp Tyr Ser Lys Tyr Leu Glu Ser
1               5                   10                  15

Ala Arg Ala Glu Ser Phe Val Lys Trp Leu Glu Ser Thr
            20                  25

<210> SEQ ID NO 18
<211> LENGTH: 29
<212> TYPE: PRT
<213> ORGANISM: Artificial sequence
<220> FEATURE:
<223> OTHER INFORMATION: Synthetic compound

<400> SEQUENCE: 18

His Ser Gln Gly Thr Phe Thr Ser Asp Tyr Ser Lys Tyr Leu Asp Leu
1               5                   10                  15

Ala Arg Ala Glu Asp Phe Val Lys Trp Leu Glu Ser Thr
            20                  25

<210> SEQ ID NO 19
<211> LENGTH: 29
<212> TYPE: PRT
<213> ORGANISM: Artificial sequence
<220> FEATURE:
<223> OTHER INFORMATION: Synthetic compound

<400> SEQUENCE: 19

His Ser Gln Gly Thr Phe Thr Ser Asp Tyr Ser Lys Tyr Leu Asp Lys
1               5                   10                  15

Arg Arg Ala Glu Asp Phe Val Ser Trp Leu Glu Ser Thr
            20                  25

<210> SEQ ID NO 20
<211> LENGTH: 29
<212> TYPE: PRT
<213> ORGANISM: Artificial sequence
<220> FEATURE:
<223> OTHER INFORMATION: Synthetic compound

<400> SEQUENCE: 20

His Ser Gln Gly Thr Phe Thr Ser Asp Tyr Ser Lys Tyr Leu Asp Val
1               5                   10                  15

Ala Arg Ala Glu Ser Phe Val Lys Trp Leu Glu Ser Thr
            20                  25

<210> SEQ ID NO 21
```

```
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 21

His Ala Gln Gly Thr Phe Thr Ser Asp Tyr Ser Lys Tyr Leu Asp Xaa
1               5                   10                  15

Ala Arg Ala Glu Ser Phe Val Lys Trp Leu Glu Ser Thr
            20                  25

<210> SEQ ID NO 22
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 22

His Ser Gln Gly Thr Phe Thr Ser Asp Tyr Ser Lys Tyr Leu Asp Xaa
1               5                   10                  15

Ala Arg Ala Glu Glu Phe Val Lys Trp Leu Glu Ser Thr
            20                  25

<210> SEQ ID NO 23
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (16)..(16)
<223> OTHER INFORMATION: Xaa is Aib

<400> SEQUENCE: 23

His Ser Gln Xaa Thr Phe Thr Ser Asp Tyr Ser Lys Tyr Leu Asp Xaa
1               5                   10                  15

Ala Arg Ala Glu Ser Phe Val Lys Trp Leu Glu Ser Thr
            20                  25

<210> SEQ ID NO 24
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 24

His Ser Gln Gly Thr Phe Thr Ser Asp Val Ser Lys Tyr Leu Asp Xaa
1               5                   10                  15
```

Ala Arg Ala Glu Ser Phe Val Lys Trp Leu Glu Ser Thr
            20                  25

<210> SEQ ID NO 25
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (3)..(3)
<223> OTHER INFORMATION: Xaa is 4-N-Acetyl-2,4-diaminobutyric acid
<220> FEATURE:
<221> NAME/KEY: MISC_FEATURE
<222> LOCATION: (16)..(16)
<223> OTHER INFORMATION: Xaa is Aib

<400> SEQUENCE: 25

His Ser Xaa Gly Thr Phe Thr Ser Asp Tyr Ser Lys Tyr Leu Asp Xaa
1               5                   10                  15

Ala Arg Ala Glu Ser Phe Val Lys Trp Leu Glu Ser Thr
            20                  25

<210> SEQ ID NO 26
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 26

His Ser Gln Gly Thr Phe Thr Ser Asp Tyr Ser Lys Tyr Leu Asp Xaa
1               5                   10                  15

Arg Arg Ala Glu Ser Phe Val Lys Trp Leu Glu Ser Thr
            20                  25

<210> SEQ ID NO 27
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (3)..(3)
<223> OTHER INFORMATION: N-delta-methyl-L-glutamine
<220> FEATURE:
<221> NAME/KEY: MISC_FEATURE
<222> LOCATION: (16)..(16)
<223> OTHER INFORMATION: Xaa is Aib

<400> SEQUENCE: 27

His Ser Xaa Gly Thr Phe Thr Ser Asp Tyr Ser Lys Tyr Leu Asp Xaa
1               5                   10                  15

Ala Arg Ala Glu Ser Phe Val Lys Trp Leu Glu Ser Thr
            20                  25

<210> SEQ ID NO 28
<211> LENGTH: 29
<212> TYPE: PRT
<213> ORGANISM: Artificial sequence
<220> FEATURE:
<223> OTHER INFORMATION: Synthetic compound -continued

```
<400> SEQUENCE: 28

His Ser Gln Gly Thr Phe Thr Ser Asp Tyr Ser Lys Tyr Leu Asp Glu
1               5                   10                  15

Ala Arg Ala Lys Ser Phe Val Glu Trp Leu Glu Lys Thr
            20                  25

<210> SEQ ID NO 29
<211> LENGTH: 29
<212> TYPE: PRT
<213> ORGANISM: Artificial sequence
<220> FEATURE:
<223> OTHER INFORMATION: Synthetic compound

<400> SEQUENCE: 29

His Ser Gln Gly Thr Phe Thr Ser Asp Tyr Ser Lys Tyr Leu Asp Glu
1               5                   10                  15

Ala Arg Ala Lys Ser Phe Val Glu Trp Leu Glu Ser Thr
            20                  25

<210> SEQ ID NO 30
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 30

His Ser Gln Gly Thr Phe Thr Ser Asp Tyr Ser Lys Tyr Leu Asp Xaa
1               5                   10                  15

Ala Arg Ala Lys Ser Phe Val Glu Trp Leu Glu Lys Thr
            20                  25

<210> SEQ ID NO 31
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 31

His Ser Gln Gly Thr Phe Thr Ser Asp Tyr Ser Lys Tyr Leu Asp Xaa
1               5                   10                  15

Ala Arg Ala Glu Ser Phe Val Lys Trp Leu Glu Ser Ala
            20                  25

<210> SEQ ID NO 32
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 32

His Ser Gln Gly Thr Phe Thr Ser Asp Tyr Ser Lys Tyr Leu Asp Xaa
```

-continued

```
1               5                   10                  15
Ala Arg Ala Glu Ser Phe Val Lys Trp Leu Glu Ser Thr
            20                  25

<210> SEQ ID NO 33
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (3)..(3)
<223> OTHER INFORMATION: Xaa is 4-N-Acetyl-2,4-diaminobutyric acid
<220> FEATURE:
<221> NAME/KEY: MISC_FEATURE
<222> LOCATION: (16)..(16)
<223> OTHER INFORMATION: Xaa is Aib

<400> SEQUENCE: 33

His Ser Xaa Gly Thr Phe Thr Ser Asp Tyr Ser Lys Tyr Leu Asp Xaa
1               5                   10                  15

Ala Arg Ala Glu Ser Phe Val Lys Trp Leu Glu Ser Thr
            20                  25

<210> SEQ ID NO 34
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 34

His Ser Gln Gly Thr Phe Thr Ser Asp Tyr Ser Lys Tyr Leu Asp Xaa
1               5                   10                  15

Ala Arg Ala Glu Glu Phe Val Ser Trp Leu Glu Lys Thr
            20                  25

<210> SEQ ID NO 35
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 35

His Ser Gln Gly Thr Phe Thr Ser Asp Tyr Ser Lys Tyr Leu Asp Xaa
1               5                   10                  15

Ala Arg Ala Glu Lys Phe Val Glu Trp Leu Glu Ser Thr
            20                  25

<210> SEQ ID NO 36
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
```

<223> OTHER INFORMATION: Xaa is Aib

<400> SEQUENCE: 36

His Ser Gln Gly Thr Phe Thr Ser Asp Tyr Ser Lys Tyr Leu Asp Xaa
1               5                   10                  15

Ala Arg Ala Glu Glu Phe Val Ala Trp Leu Glu Ser Thr
            20                  25

<210> SEQ ID NO 37
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 37

His Ser Gln Gly Thr Phe Thr Ser Asp Tyr Ser Lys Tyr Leu Asp Xaa
1               5                   10                  15

Ala Arg Ala Glu Glu Phe Val Lys Trp Leu Glu Glu Thr
            20                  25

<210> SEQ ID NO 38
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 38

His Ser Gln Gly Thr Phe Thr Ser Asp Tyr Ser Lys Tyr Leu Glu Xaa
1               5                   10                  15

Ala Arg Ala Glu Glu Phe Val Lys Trp Leu Glu Ser Thr
            20                  25

<210> SEQ ID NO 39
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 39

His Ser His Gly Thr Phe Thr Ser Asp Tyr Ser Lys Tyr Leu Asp Xaa
1               5                   10                  15

Ala Arg Ala Glu Glu Phe Val Lys Trp Leu Glu Ser Thr
            20                  25

<210> SEQ ID NO 40
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE -continued

```
<222> LOCATION: (3)..(3)
<223> OTHER INFORMATION: Xaa is 4-N-Acetyl-2,4-diaminobutyric acid
<220> FEATURE:
<221> NAME/KEY: MISC_FEATURE
<222> LOCATION: (16)..(16)
<223> OTHER INFORMATION: Xaa is Aib

<400> SEQUENCE: 40

His Ser Xaa Gly Thr Phe Thr Ser Asp Tyr Ser Lys Tyr Leu Asp Xaa
1               5                   10                  15

Ala Arg Ala Glu Glu Phe Val Lys Trp Leu Glu Ser Thr
            20                  25

<210> SEQ ID NO 41
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (3)..(3)
<223> OTHER INFORMATION: Xaa is 3-N-Acetyl-2,3-diaminopropionic acid
<220> FEATURE:
<221> NAME/KEY: MISC_FEATURE
<222> LOCATION: (16)..(16)
<223> OTHER INFORMATION: Xaa is Aib

<400> SEQUENCE: 41

His Ser Xaa Gly Thr Phe Thr Ser Asp Tyr Ser Lys Tyr Leu Asp Xaa
1               5                   10                  15

Ala Arg Ala Glu Glu Phe Val Lys Trp Leu Glu Ser Thr
            20                  25

<210> SEQ ID NO 42
<211> LENGTH: 29
<212> TYPE: PRT
<213> ORGANISM: Artificial sequence
<220> FEATURE:
<223> OTHER INFORMATION: Synthetic compound

<400> SEQUENCE: 42

His Ser Gln Gly Thr Phe Thr Ser Asp Tyr Ser Lys Tyr Leu Asp Ser
1               5                   10                  15

Ala Arg Ala Glu Asp Phe Val Lys Trp Leu Glu Ser Thr
            20                  25

<210> SEQ ID NO 43
<211> LENGTH: 29
<212> TYPE: PRT
<213> ORGANISM: Artificial sequence
<220> FEATURE:
<223> OTHER INFORMATION: Synthetic compound

<400> SEQUENCE: 43

His Ser Gln Gly Thr Phe Thr Ser Asp Tyr Ser Lys Tyr Leu Glu Ser
1               5                   10                  15

Arg Arg Ala Lys Glu Phe Val Glu Trp Leu Glu Ser Thr
            20                  25

<210> SEQ ID NO 44
<211> LENGTH: 29
<212> TYPE: PRT
<213> ORGANISM: Artificial Sequence
<220> FEATURE:
<223> OTHER INFORMATION: synthetic construct
```

```
<400> SEQUENCE: 44

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Glu Asn Thr
            20                  25
```

GLUCAGON ANALOGUES

SEQUENCE LISTING

The instant application contains a Sequence Listing which has been submitted electronically in ASCII format and is hereby incorporated by reference in its entirety. Said ASCII copy, created on Sep. 10, 2019 is named "50412-094002 Sequence Listing" and is 18,221 bytes in size.

FIELD OF THE INVENTION

The present invention relates to glucagon analogues and their medical use, for example in the treatment of hypoglycaemia. In particular, the present invention relates to stable glucagon analogues suitable for use in a liquid formulation.

BACKGROUND OF THE INVENTION

Human preproglucagon is a 158 amino acid precursor polypeptide that is differentially processed in the tissues to form a number of structurally related proglucagon-derived peptides, including glucagon (Glu or GCG), glucagon-like peptide-1 (GLP-1), glucagon-like peptide-2 (GLP-2), and oxyntomodulin (OXM). These molecules are involved in a wide variety of physiological functions, including glucose homeostasis, insulin secretion, gastric emptying and intestinal growth, as well as regulation of food intake.

Native glucagon is a 29-amino acid peptide that corresponds to amino acids 53 to 81 of preproglucagon. Glucagon helps maintain the level of glucose in the blood by binding to glucagon receptors on hepatocytes, causing the liver to release glucose—stored in the form of glycogen—through glycogenolysis. As these stores become depleted, glucagon also stimulates the liver to synthesize additional glucose by gluconeogenesis. This glucose is released into the bloodstream, preventing the development of hypoglycaemia.

Owing to the relatively low physical and chemical stability of native glucagon per se, glucagon products that are currently available commercially, and which are intended primarily for use in "rescue" situations for alleviating acute hypoglycaemia in a diabetic subject who has received an excessively high dose of insulin, are provided in the form of freeze-dried, solid preparations intended for reconstitution in an appropriate liquid medium immediately before use. Hypoglycemic subjects may, inter alia, exhibit dizziness and/or confusion, and in some cases may become unconscious or semi-conscious, rendering them unable to carry out or complete the required initial liquid reconstitution and subsequent injection of the glucagon formulation in question. As a result, this reconstitution and injection may have to be performed by another person who is not experienced in processing the product in the limited time available before excessive glucagon aggregation occurs.

Although stabilized analogues of native glucagon in liquid solution are desirable, no stable liquid formulation of any such glucagon analogue is commercially available.

On that basis, it is clear that there is a strong need for glucagon analogues that, in addition to having satisfactorily high activity at the glucagon receptor, are sufficiently soluble (especially at physiological pH, where native glucagon is not) and stable (both physically and chemically) in aqueous liquid medium. These analogues (i) may advantageously be provided in the form of a ready-to-use liquid pharmaceutical formulation adapted for immediate injection, and (ii) may be able to be stored (including carried by the subject or patient in question under ambient conditions) for a satisfactorily long period of time prior to use.

SUMMARY OF THE INVENTION

In some embodiments, the present invention provides a compound having the formula I:

$$R^1\text{—}Z\text{—}R^2 \quad (I)$$

or a pharmaceutically acceptable salt or solvate thereof; wherein $R^1$ is hydrogen, $C_{1-4}$ alkyl, acetyl, formyl, benzoyl or trifluoroacetyl;

$R^2$ is OH or $NH_2$; and

Z is an amino acid sequence deriving from the sequence of formula Ia:

(Ia)
(SEQ ID NO: 44)
His-Ser-Gln-Gly-Thr-Phe-Thr-Ser-Asp-Tyr-Ser-Lys-

Tyr-Leu-Asp-Ser-Arg-Arg-Ala-Gln-Asp-Phe-Val-Gln-

Trp-Leu-Glu-Asn-Thr and further comprising at least four amino acid substitutions or deletions that are only at amino acid sequence positions (designated by an X) selected from 2, 3, 4, 9, 10, 15, 16, 17, 20, 21, 24, 28 and 29, as follows:

X2 is selected from Aib and Ala;

X3 is selected from His, Pro, Dab(Ac), Dap(Ac) and Gln(Me);

X4 is DAla;

X9 is Glu;

X10 is selected from Val, Leu, N-Me-Tyr and N-Me-DTyr;

X15 is Glu;

X16 is selected from Aib, Lys, Glu, Leu, Val, DVal, Phe, His, Arg, Pro, DPro, N-Me-Ser and N-Me-DSer;

X17 is selected from Ala and Ser;

X20 is selected from Glu and Lys;

X21 is selected from Glu, Lys and Ser;

X24 is selected from Lys, Ser, Glu and Ala;

X28 is selected from Ser, Glu, and Lys, or is absent;

X29 is selected from Ser and Ala, or is absent;

with the proviso that Z is not selected from:

(SEQ ID NO: 42)
HSQGTFTSDYSKYLDSARAEDFVKWLEST;
and (SEQ ID NO: 43)
HSQGTFTSDYSKYLESRRAKEFVEWLEST.

In some embodiments, the present invention provides a compound having the formula I:

$$R^1\text{—}Z\text{—}R^2 \quad (I)$$

or a pharmaceutically acceptable salt or solvate thereof; wherein $R^1$ is hydrogen, $C_{1-4}$ alkyl, acetyl, formyl, benzoyl or trifluoroacetyl;

R² is OH or NH₂; and

Z is an amino acid sequence deriving from the sequence of formula Ia:

(Ia)
(SEQ ID NO: 44)
His-Ser-Gln-Gly-Thr-Phe-Thr-Ser-Asp-Tyr-Ser-Lys-

Tyr-Leu-Asp-Ser-Arg-Arg-Ala-Gln-Asp-Phe-Val-Gln-

Trp-Leu-Glu-Asn-Thr and further comprising at least four amino acid substitutions or deletions that are only at amino acid sequence positions selected from 2, 3, 9, 10, 15, 16, 17, 20, 21, 24, 28 and 29, as follows:

X2 is selected from Aib and Ala;
X3 is selected from His and Pro;
X9 is Glu;
X10 is selected from N-Me-Tyr and N-Me-DTyr;
X15 is Glu;
X16 is selected from Aib, Lys, Glu, Leu, Val, DVal, Phe, His, Arg, Pro, DPro, N-Me-Ser and N-Me-DSer;
X17 is selected from Ala and Ser;
X20 is selected from Glu and Lys;
X21 is selected from Glu, Lys and Ser;
X24 is selected from Lys, Ser, Glu and Ala;
X28 is selected from Ser and Lys, or is absent;
X29 is selected from Ser and Ala, or is absent;
with the proviso that Z is not selected from:

(SEQ ID NO: 42)
HSQGTFTSDYSKYLDSARAEDFVKWLEST;
and (SEQ ID NO: 43)
HSQGTFTSDYSKYLESRRAKEFVEWLEST.

In some embodiments, the at least four amino acid substitutions or deletions at amino acid sequence positions (designated by an X) selected from 2, 3, 4, 9, 10, 15, 16, 17, 20, 21, 24, 28 and 29 of the compound of formula I are as follows:

X2 is selected from Aib and Ala;
X3 is selected from His and Pro, Dab(Ac), Dap(Ac) and Gln(Me);
X4 is DAla;
X9 is Glu;
X10 is selected from Val, Leu, N-Me-Tyr and N-Me-DTyr;
X15 is Glu;
X16 is selected from Aib, Lys, Glu, Leu, Val, Phe, His and Arg;
X17 is selected from Ala and Ser;
X20 is selected from Glu and Lys;
X21 is selected from Glu, Lys and Ser;
X24 is selected from Lys, Ser, Glu and Ala;
X28 is selected from Ser, Glu, and Lys, or is absent;
X29 is selected from Ser and Ala, or is absent.

In some embodiments, the at least four amino acid substitutions or deletions are at amino acid sequence positions (designated by an X) selected from 2, 3, 4, 10, 15, 16, 17, 20, 21, 24, 28 and 29 of the compound of formula I, and are as follows:

X2 is Ala;
X3 is Dab(Ac), Dap(Ac) and Gln(Me);
X4 is DAla;
X10 is selected from Leu and Val;
X15 is Glu;
X16 is selected from Aib, Lys, Glu, Leu, and Val;
X17 is Ala;
X20 is selected from Glu and Lys;
X21 is selected from Glu and Ser;
X24 is selected from Lys, Ser and Glu;
X28 is selected from Ser, Glu and Lys;
X29 is Ala, or is absent.

In some embodiments, the at least four amino acid substitutions or deletions are at amino acid sequence positions (designated by an X) selected from 2, 3, 4, 16, 17, 20, 21, 24, 28 and 29 of the compound of formula I, and are as follows:

X2 is Ala;
X3 is Dab(Ac), Dap(Ac), Gln(Me) or His;
X4 is DAla;
X16 is selected from Aib, Lys, Glu;
X17 is Ala;
X20 is selected from Glu and Lys;
X21 is selected from Glu and Ser;
X24 is selected from Lys, Ser and Glu;
X28 is selected from Ser, Glu and Lys;
X29 is Ala, or is absent.

It will be understood that any individual molecule comprises at least 4 differences from the sequence of formula Ia, which may be any combination of at least 4 substitutions and deletions permitted within the definitions provided.

The peptide sequence Z may have a maximum of 4 substitutions and deletions (taken in combination), a maximum of 5 substitutions and deletions, a maximum of 6 substitutions and deletions, a maximum of 7 substitutions and deletions, a maximum of 8 substitutions and deletions, a maximum of 9 substitutions and deletions, a maximum of 10 substitutions and deletions, a maximum of 11 substitutions and deletions, a maximum of 12 substitutions and deletions, or a maximum of 13 substitutions and deletions compared to the amino acid sequence of Formula Ia.

For example, the compounds may have between 4 and 11 substitutions and deletions, between 6 and 11 substitutions and deletions, between 4 and 9 substitutions and deletions, or between 6 and 9 substitutions and deletions.

The compounds of the invention have glucagon agonist activity.

The compounds of the invention have improved solubility and/or stability as compared to native human glucagon.

Improved solubility may comprise or constitute improved solubility compared to native glucagon at pH 4 (e.g. in 100 mM acetate buffer at pH 4), pH 5 (e.g. in 100 mM acetate buffer at pH 5), pH 6 (e.g. in 100 mM phosphate buffer at pH 6), pH 7 (e.g. in 100 mM phosphate buffer at pH 7), and/or pH 7.5 (e.g. in 100 mM phosphate buffer at pH 7.5). The determination may be performed under the conditions set out in Example 4. A solubility of ≥1 mg/ml may be desirable.

Improved stability may comprise or constitute improved physical stability and/or improved chemical stability as compared to native human glucagon.

Improved physical stability may comprise or constitute reduced tendency to aggregate, e.g. to form either soluble or insoluble aggregates, e.g. fibrils. Aggregation (e.g. fibril formation) may be determined, for example, at a starting concentration of 1 mg/ml dissolved peptide at pH 7.5 and 40° C. Any appropriate time period may be used, e.g. 24 hours, 48 hours or 96 hours. Aggregation may be determined under the conditions set out in Example 5, with or without agitation.

Improved chemical stability may comprise or constitute a reduced tendency to peptide cleavage or degradation in aqueous buffer, typically in the absence of contaminating protease or peptidase activity. Stability may be determined, for example, at a starting concentration of 1 mg/ml dissolved peptide at pH 4.0 or 7.5 and 40° C. The assessment may comprise determining intact peptide remaining after incubation for a suitable time period. This may involve determining intact peptide purity as defined in Example 6. Incubation may be performed for any suitable time period, e.g. 1 day, 7 days or 14 days. Stability may be determined under the conditions set out in Example 6.

Further embodiments of the present invention include, but are not limited to:

a compound, or a pharmaceutically acceptable salt or solvate thereof, of the invention for use in therapy (e.g. in the treatment of acute or chronic hypoglycaemia);

a pharmaceutical composition comprising a compound, or a pharmaceutically acceptable salt or solvate thereof, of the invention and a pharmaceutically acceptable carrier;

a method of treating a disease or condition in a subject in need thereof, the method comprising administering a therapeutically effective amount of a compound, or a pharmaceutically acceptable salt or solvate thereof, of the invention, or a pharmaceutical composition of the invention to the subject;

use of a compound, or a salt or solvate thereof, of the invention, or a pharmaceutical composition of the invention, in the manufacture of a medicament for use in therapy (e.g. in treatment of acute or chronic hypoglycaemia);

a nucleic acid construct (e.g., a DNA or RNA construct) encoding a compound (peptide) or a peptide Z of the invention;

an expression vector comprising such a nucleic acid construct of the invention; and a host cell comprising such a nucleic acid construct or expression vector of the invention.

In some embodiments, a disease or condition to be treated with a compound or method of the invention is selected from the group consisting of: hypoglycaemia, acute hypoglycaemia, chronic hypoglycaemia, type 2 diabetes, impaired glucose tolerance, type 1 diabetes, obesity, coronary heart disease, atherosclerosis, hypertension, dyslipidemia, hepatic steatosis, β-blocker poisoning, insulinoma, and Von Gierkes disease. In particular embodiments, the disease or condition is hypoglycaemia. In certain embodiments, the hypoglycaemia is selected from the group consisting of: diabetic hypoglycaemia, acute insulin-induced hypoglycaemia, non-diabetic hypoglycaemia, reactive hypoglycaemia, fasting hypoglycaemia, drug-induced hypoglycaemia, alcohol-induced hypoglycaemia, gastric bypass-induced hypoglycaemia, and hypoglycaemia occurring during pregnancy.

In some embodiments, the invention includes a compound or pharmaceutically acceptable salt or solvate thereof for the treatment of hypoglycaemia.

BRIEF DESCRIPTION OF THE DRAWINGS

FIG. 1 is a graph showing the effect of a single subcutaneous administration of vehicle (PBS, pH 7.4), human glucagon (20 nmol/kg body weight) or Compound 14 of the invention (20 and 60 nmol/kg body weight), respectively, on blood glucose levels for 120 minutes in anaesthetized, 5-hour-fasted euglycemic male Sprague-Dawley rats. Data are mean values with SEM (n=6/group).

DETAILED DESCRIPTION OF THE INVENTION

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well known and commonly used in the art.

All publications, patents and published patent applications referred to in this application are specifically incorporated by reference herein. In case of conflict, the present specification, including its specific definitions, will control.

Each embodiment of the invention described herein may be taken alone or in combination with one or more other embodiments of the invention.

Definitions

Unless specified otherwise, the following definitions are provided for specific terms, which are used herein.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

In addition to the explanations of the meanings of certain terms or expressions employed in the present specification that are provided in the above, the following definitions/explanations also apply:

The term "pharmaceutically acceptable carrier" includes any of the standard pharmaceutical carriers or diluents, such as those used in compositions or formulations suitable for oral, pulmonary, rectal, nasal, topical, subcutaneous, intramuscular, intravenous, intraperitoneal, intradermal, transdermal or vaginal administration. Pharmaceutically acceptable carriers for therapeutic use are well known in the pharmaceutical art, and are described, for example, in *Remington's Pharmaceutical Sciences*, Mack Publishing Co. (A. R. Gennaro edit. 1985). Liquid compositions often employ unbuffered or buffered aqueous solutions as carriers. For example, sterile saline or phosphate-buffered saline (PBS) at slightly acidic, slightly alkaline or physiological pH may be used. Relevant pH-buffering agents (some of which have already been mentioned above in connection with pharmaceutical compositions) include phosphates, citrate, acetate, tris(hydroxymethyl)aminomethane (TRIS), N-tris(hydroxymethyl)methyl-3-aminopropane-sulfonic acid (TAPS), ammonium bicarbonate, diethanolamine, histidine (which is often a preferred buffer), arginine and lysine, as well as mixtures thereof. The term further encompasses any agents listed in the US Pharmacopeia for use in animals or humans.

The term "pharmaceutically acceptable salt" in the context of the invention refers to a salt that is not harmful to the patient or subject to be treated therewith. Such salts are in general acid addition salts or basic salts. Acid addition salts include salts of inorganic acids and salts of organic acids.

Non-limiting examples of suitable acid addition salts include hydrochloride salts, phosphate salts, formate salts, acetate salts, trifluoroacetate salts and citrate salts. Examples of basic salts include salts where the cation is selected from alkali metal ions, such as sodium and potassium, alkaline earth metal ions, such as calcium, as well as substituted ammonium ions, e.g. of the type $NR(R')_3^+$, where R and R' independently designate optionally substituted $C_{1-6}$alkyl, optionally substituted $C_{2-6}$ alkenyl, optionally substituted aryl, or optionally substituted heteroaryl. Other examples of pharmaceutically acceptable salts are described in *Remington's Pharmaceutical Sciences,* 17th edition. Ed. Alfonso R. Gennaro (Ed.), Mack Publishing Company, Easton, Pa., U.S.A., 1985 and more recent editions, and in the *Encyclopaedia of Pharmaceutical Technology.*

The term "solvate" in the context of the present invention refers to a complex of defined stoichiometry formed by a solute (in casu a compound, or a pharmaceutically acceptable salt thereof, of the present invention) and a solvent. Relevant solvents (particularly in the case of pharmaceutically acceptable solvates) include, but are not limited to, water, ethanol and acetic acid. Solvates in which the solvent molecule in question is water are generally referred to as "hydrates".

The terms "therapeutically effective amount" and "therapeutically effective dose" as employed in the context of the present invention (notably in the context of a compound of the invention) refer to an amount or a dose sufficient to cure, alleviate, partially arrest or otherwise promote the cure or healing of a given condition (disorder, disease) or injury and, preferably, complications arising therefrom. An amount or dose effective for a particular purpose will depend on the severity of the condition or injury as well as on the body weight and general state of the subject or patient to be treated. Determination of an amount or dose that is appropriate is within the skills of a trained physician (or veterinarian) of ordinary skill.

The term "treatment" (as well as "treating" and other grammatical variants thereof) as employed in the context of the invention refers to an approach for obtaining beneficial or desired clinical results. For the purposes of the present invention, beneficial or desired clinical results include, but are not limited to, alleviation of symptoms, diminishment of extent of disease, stabilization of (i.e. not worsening of) state of disease, delay or slowing of disease progression, amelioration or palliation of disease state, and remission (whether partial or total), whether detectable or undetectable. "Treatment" may also refer to prolongation of survival compared to expected survival in the absence of treatment. "Treatment" is an intervention performed with the intention of preventing the development of, or altering the pathology of, a disorder. Accordingly, "treatment" refers both to therapeutic treatment and to prophylactic or preventative measures. As used in the context of prophylactic or preventative measures, the compound need not completely prevent the development of the disease or disorder. Those in need of treatment include those already suffering from the disorder, as well as those in which development of the disorder is to be prevented. "Treatment" also means inhibition or reduction of an increase in pathology or symptoms (e.g. weight gain or hypoglycaemia) compared to the absence of treatment, and is not necessarily meant to imply complete cessation of the relevant condition.

The term "agonist" as employed in the context of the invention refers to a substance (ligand) that activates the receptor type in question.

Throughout the present specification, the conventional one-letter and three-letter codes for naturally occurring amino acids are used. Unless otherwise indicated, reference is made to the L-isomeric forms of the amino acids referred to herein.

Dab(Ac): 4-N-Acetyl-2,4-diaminobutyric acid, (2S)-4-(Acetylamino)-2-aminobutanoic acid or 4-(acetylamino)-2-aminobutanoic acid (L-form).

Dap(Ac): 3-N-Acetyl-2,3-diaminopropionic acid or 3-(acetylamino)-2-aminopropanoic acid (L-form)

Gln(Me): N-δ-methyl-L-glutamine

N-Me-Tyr: Tyrosine which is methylated at the α-nitrogen

N-Me-DTyr: D-Tyrosine which is methylated at the α-nitrogen

N-Me-Ser: Serine which is methylated at the α-nitrogen

N-Me-DSer: D-Serine which is methylated at the α-nitrogen

Aib: α-aminoisobutyric acid

The term "native glucagon" refers to native human glucagon having the sequence Hy-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH (SEQ ID NO: 1).

Among sequences disclosed herein are sequences incorporating an "Hy-" moiety at the amino terminus (N-terminus) of the sequence, and either an "—OH" moiety or an "—$NH_2$" moiety at the carboxy terminus (C-terminus) of the sequence. In such cases, and unless otherwise indicated, an "Hy-" moiety at the N-terminus of the sequence in question indicates a hydrogen atom [i.e. $R^1$=hydrogen=Hy- in formulas I and Ia; corresponding to the presence of a free primary or secondary amino group at the N-terminus], while an "—OH" or an "—$NH_2$" moiety at the C-terminus of the sequence indicates a hydroxy group [e.g., $R^2$=OH in formulas I and Ia; corresponding to the presence of a carboxy (COOH) group at the C-terminus] or an amino group [e.g., $R^2$=$NH_2$ in formulas I and Ia; corresponding to the presence of an amido ($CONH_2$) group at the C-terminus], respectively. In each sequence of the invention, a C-terminal "—OH" moiety may be substituted for a C-terminal "—$NH_2$" moiety, and vice-versa.

Some embodiments of the present invention relate to compounds having the formula I:

$$R^1\text{—}Z\text{—}R^2 \tag{I}$$

or a pharmaceutically acceptable salt or solvate thereof; wherein $R^1$ is hydrogen-, $C_{1-4}$ alkyl, acetyl, formyl, benzoyl or trifluoroacetyl;

$R^2$ is —OH or —$NH_2$; and

Z is an amino acid sequence deriving from the sequence of formula Ia:

(Ia)
(SEQ ID NO: 44)
His-Ser-Gln-Gly-Thr-Phe-Thr-Ser-Asp-Tyr-Ser-Lys-

Tyr-Leu-Asp-Ser-Arg-Arg-Ala-Gln-Asp-Phe-Val-Gln-

Trp-Leu-Glu-Asn-Thr and further comprising at least four amino acid substitutions or deletions that are only at sequence positions (designated by an X) selected from 2, 3, 4, 9, 10, 15, 16, 17, 20, 21, 24, 28 and 29, as follows:

X2 is selected from Aib and Ala;
X3 is selected from His, Pro, Dab(Ac), Dap(Ac) and Gln(Me);
X4 is DAla;
X9 is Glu;
X10 is selected from Val, Leu N-Me-Tyr and N-Me-DTyr;
X15 is Glu;
X16 is selected from Aib, Lys, Glu, Leu, Val, DVal, Phe, His, Arg, Pro, DPro, N-Me-Ser and N-Me-DSer;
X17 is selected from Ala and Ser;
X20 is selected from Glu and Lys;
X21 is selected from Glu, Lys and Ser;
X24 is selected from Lys, Ser, Glu and Ala;
X25 is selected from Arg, Lys, His, Ile, Leu, Ala, Met, Cys, Asn, Val, Ser, Glu, Asp, Gln, Thr and (p)Tyr;
X28 is selected from Ser, Lys, and Glu, or is absent;
X29 is selected from Ser and Ala, or is absent; with the proviso that Z is not selected from:

```
                                         (SEQ ID NO: 42)
HSQGTFTSDYSKYLDSARAEDFVKWLEST;
and
                                         (SEQ ID NO: 43)
HSQGTFTSDYSKYLESRRAKEFVEWLEST.
```

Some embodiments of the present invention relate to compounds having the formula I:
R¹—Z—R² (I)
or a pharmaceutically acceptable salt or solvate thereof; wherein
R¹ is hydrogen-, $C_{1-4}$ alkyl, acetyl, formyl, benzoyl or trifluoroacetyl;
R² is —OH or —$NH_2$; and
Z is an amino acid sequence deriving from the sequence of formula Ia:

```
(Ia)
                                         (SEQ ID NO: 44)
His-Ser-Gln-Gly-Thr-Phe-Thr-Ser-Asp-Tyr-Ser-Lys-

Tyr-Leu-Asp-Ser-Arg-Arg-Ala-Gln-Asp-Phe-Val-Gln-

Trp-Leu-Glu-Asn-Thr
``` and further comprising at least four amino acid substitutions or deletions that are only at sequence positions (designated by an X) selected from 2, 3, 9, 10, 15, 16, 17, 20, 21, 24, 28 and 29, as follows:

X2 is selected from Aib and Ala;
X3 is selected from His and Pro;
X9 is Glu;
X10 is selected from N-Me-Tyr and N-Me-DTyr;
X15 is Glu;
X16 is selected from Aib, Lys, Glu, Leu, Val, DVal, Phe, His, Arg, Pro, DPro, N-Me-Ser and N-Me-DSer;
X17 is selected from Ala and Ser;
X20 is selected from Glu and Lys;
X21 is selected from Glu, Lys and Ser;
X24 is selected from Lys, Ser, Glu and Ala;
X25 is selected from Arg, Lys, His, Ile, Leu, Ala, Met, Cys, Asn, Val, Ser, Glu, Asp, Gln, Thr and (p)Tyr;
X28 is selected from Ser and Lys, or is absent;
X29 is selected from Ser and Ala, or is absent;

with the proviso that Z is not selected from:

```
                                         (SEQ ID NO: 42)
HSQGTFTSDYSKYLDSARAEDFVKWLEST;
and
                                         (SEQ ID NO: 43)
HSQGTFTSDYSKYLESRRAKEFVEWLEST.
```

In some embodiments, the at least four amino acid substitutions or deletions at amino acid sequence positions (designated by an X) selected from 2, 3, 4, 9, 10, 15, 16, 17, 20, 21, 24, 28 and 29 of the compound of formula I are as follows:

X2 is selected from Aib and Ala;
X3 is selected from His and Pro, Dab(Ac), Dap(Ac) and Gln(Me);
X4 is DAla;
X9 is Glu;
X10 is selected from Val, Leu, N-Me-Tyr and N-Me-DTyr;
X15 is Glu;
X16 is selected from Aib, Lys, Glu, Leu, Val, Phe, His and Arg;
X17 is selected from Ala and Ser;
X20 is selected from Glu and Lys;
X21 is selected from Glu, Lys and Ser;
X24 is selected from Lys, Ser, Glu and Ala;
X28 is selected from Ser, Glu and Lys, or is absent;
X29 is selected from Ser and Ala, or is absent.

In some embodiments, the at least four amino acid substitutions or deletions are at amino acid sequence positions (designated by an X) selected from 2, 3, 4, 10, 15, 16, 17, 20, 21, 24, 28 and 29 of the compound of formula I, and are as follows:

X2 is Ala;
X3 is Dab(Ac) and Gln(Me);
X4 is DAla;
X10 is selected from Leu and Val;
X15 is Glu;
X16 is selected from Aib, Lys, Glu, Leu, and Val;
X17 is Ala;
X20 is selected from Glu and Lys;
X21 is selected from Glu and Ser;
X24 is selected from Lys, Ser and Glu;
X28 is selected from Ser, Glu and Lys;
X29 is Ala, or is absent. In some embodiments, X3 is selected from Dab(Ac) and Gln(Me).

In some embodiments, the at least four amino acid substitutions or deletions are at amino acid sequence positions (designated by an X) selected from 2, 3, 4, 16, 17, 20, 21, 24, 28 and 29 of the compound of formula I, and are as follows:

X2 is Ala;
X3 is Dab(Ac), Dap(Ac), Gln(Me) or His;
X4 is DAla;
X16 is selected from Aib, Lys, Glu;
X17 is Ala;
X20 is selected from Glu and Lys;
X21 is selected from Glu and Ser;
X24 is selected from Lys, Ser and Glu;
X28 is selected from Ser, Glu and Lys;
X29 is Ala, or is absent.
In some embodiments, X17 is Ala.

In some embodiments, X25 is selected from Arg, His or Lys. In some embodiments, the compounds of the invention may comprise substitutions in position 25, such as those referred to in WO2011/117417, which is incorporated herein by reference. However, such substitutions at position 25 are not necessary in the present invention to obtain enhanced physical stability of the glucagon analogues.

In some embodiments, X27 is selected from Ser, Lys, Glu, and Asp. In some embodiments, X27 is selected from: Glu and Asp. In some embodiments, X27 is Glu.

In some embodiments, X28 and/or X29 may be amino acid residues other than those disclosed above. In some embodiments, the substitution may be a hydrophilic substitution (e.g., Arg, Lys, Asn, His, Gln, Asp, Ser, or Glu). In some embodiments, X28 and/or X29 may be selected from: Glu, Asp, Lys, Arg, Ser, Leu, Ala and Gly. In some embodiments, X28 is Glu or Asp. In some embodiments, X29 is Glu or Asp. In some embodiments, X28 is Glu and X29 is Glu.

In some embodiments, X17 is Ala and X27 is Glu. In some embodiments, X20 is Glu and X27 is Glu. In some embodiments, X17 is Ala, X20 is Glu, and X27 is Glu. In some embodiments, X16 is Aib and X27 is Glu. In some embodiments, X16 is Aib, X21 is Ser, and X27 is Glu. In some embodiments, X16 is Aib, X21 is Ser, X27 is Glu, and X28 is Ser.

In addition to the possibility of substitution of the amino acid residue at position 3 (X3) in formula Ia with an amino acid residue selected from His, Pro, Dab(Ac) and Gln(Me), position 3 may also be substituted with an analogue of glutamine, which will typically be an unnatural amino acid (i.e. one not naturally occurring in mammalian proteins) such as Dap(Ac) [i.e. X3=Dap(Ac)]. Nonetheless, in all of the definitions provided herein, the invention further encompasses compounds defined by the same generic formulae but in which Dap(Ac) is not permitted at X3.

In some embodiments of compounds of the invention, Z is selected from the group consisting of:

```
                                        (SEQ ID NO: 2)
HSQGTFTSDYSKYLDSARAESFVKWLEST (SEQ ID NO: 3)
HSQGTFTSDYSKYLDSARAEDFVKWLEET (SEQ ID NO: 4)
HSQGTFTSDYSKYLDKARAEDFVKWLEST (SEQ ID NO: 5)
HSQGTFTSDYSKYLDSARAEDFVAWLEST (SEQ ID NO: 6)
HSQGTFTSDYSKYLDEARAKDFVEWLEKT (SEQ ID NO: 7)
HSQGTFTSDYSKYLDSARAEDFVEWLEST (SEQ ID NO: 8)
HSQGTFTSDYSRYLESARAEDFVKWLEST (SEQ ID NO: 9)
HSQGTFTSDYSKYLESARAEDFVKWLEST (SEQ ID NO: 10)
HSQGTFTSDYSKYLDSARAEEFVKWLEST (SEQ ID NO: 11)
HSQGTFTSDYSKYLDSARAEDFVSWLEST (SEQ ID NO: 12)
HSQGTFTSDLSKYLDSARAEDFVKWLEST (SEQ ID NO: 13)
HSQGTFTSDYSKYLD-Aib-ARAEDFVKWLEST (SEQ ID NO: 14)
HSQGTFTSDYSKYLDSARAEDFVKWLES (SEQ ID NO: 15)
HSQGTFTSDYSKYLDEARAEDFVKWLEST (SEQ ID NO: 16)
HSQGTFTSDYSKYLD-Aib-ARAESFVKWLEST (SEQ ID NO: 17)
HSQGTFTSDYSKYLESARAESFVKWLEST (SEQ ID NO: 18)
HSQGTFTSDYSKYLDLARAEDFVKWLEST (SEQ ID NO: 19)
HSQGTFTSDYSKYLDKRRAEDFVSWLEST (SEQ ID NO: 20)
HSQGTFTSDYSKYLDVARAESFVKWLEST (SEQ ID NO: 21)
HAQGTFTSDYSKYLD-Aib-ARAESFVKWLEST (SEQ ID NO: 22)
HSQGTFTSDYSKYLD-Aib-ARAEEFVKWLEST (SEQ ID NO: 23)
HSQ-DAla-TFTSDYSKYLD-Aib-ARAESFVKWLEST (SEQ ID NO: 24)
HSQGTFTSDVSKYLD-Aib-ARAESFVKWLEST (SEQ ID NO: 25)
HS-[Dab(Ac)]-GTFTSDYSKYLD-Aib-ARAESFVKWLEST (SEQ ID NO: 26)
HSQGTFTSDYSKYLD-Aib-RRAESFVKWLEST (SEQ ID NO: 27)
HS-[Gln(Me)]-GTFTSDYSKYLD-Aib-ARAESFVKWLEST (SEQ ID NO: 28)
HSQGTFTSDYSKYLDEARAKSFVEWLEKT (SEQ ID NO: 29)
HSQGTFTSDYSKYLDEARAKSFVEWLEST (SEQ ID NO: 30)
HSQGTFTSDYSKYLD-Aib-ARAKSFVEWLEKT (SEQ ID NO: 31)
HSQGTFTSDYSKYLD-Aib-ARAESFVKWLESA (SEQ ID NO: 32)
HSQGTFTSDYSKYLD-Aib-ARAESFVKWLEST (SEQ ID NO: 33)
HS-[Dab(Ac)]-GTFTSDYSKYLD-Aib-ARAESFVKWLEST (SEQ ID NO: 34)
HSQGTFTSDYSKYLD-Aib-ARAEEFVSWLEKT (SEQ ID NO: 35)
HSQGTFTSDYSKYLD-Aib-ARAEKFVEWLEST (SEQ ID NO: 36)
HSQGTFTSDYSKYLD-Aib-ARAEEFVAWLEST (SEQ ID NO: 37)
HSQGTFTSDYSKYLD-Aib-ARAEEFVKWLEET (SEQ ID NO: 38)
HSQGTFTSDYSKYLE-Aib-ARAEEFVKWLEST
```

```
                                          (SEQ ID NO: 39)
HSHGTFTSDYSKYLD-Aib-ARAEEFVKWLEST (SEQ ID NO: 40)
HS-[Dab(Ac)]-GTFTSDYSKYLD-Aib-ARAEEFVKWLEST
and (SEQ ID NO: 41)
HS-[Dap(Ac)]-GTFTSDYSKYLD-Aib-ARAEEFVKWLEST.
```

Specific compounds of the invention include:

```
                                          (SEQ ID NO: 2)
Hy-HSQGTFTSDYSKYLDSARAESFVKWLEST-OH
Compound 1;

(SEQ ID NO: 3)
Hy-HSQGTFTSDYSKYLDSARAEDFVKWLEET-OH
Compound 2;

(SEQ ID NO: 4)
Hy-HSQGTFTSDYSKYLDKARAEDFVKWLEST-OH
Compound 3;

(SEQ ID NO: 5)
Hy-HSQGTFTSDYSKYLDSARAEDFVAWLEST-OH
Compound 4;

(SEQ ID NO: 6)
Hy-HSQGTFTSDYSKYLDEARAKDFVEWLEKT-OH
Compound 5;

(SEQ ID NO: 7)
Hy-HSQGTFTSDYSKYLDSARAEDFVEWLEST-OH
Compound 6;

(SEQ ID NO: 8)
Hy-HSQGTFTSDYSRYLESARAEDFVKWLEST-OH
Compound 7;

(SEQ ID NO: 9)
Hy-HSQGTFTSDYSKYLESARAEDFVKWLEST-OH
Compound 8;

(SEQ ID NO: 10)
Hy-HSQGTFTSDYSKYLDSARAEEFVKWLEST-OH
Compound 9;

(SEQ ID NO: 11)
Hy-HSQGTFTSDYSKYLDSARAEDFVSWLEST-OH
Compound 10;

(SEQ ID NO: 12)
Hy-HSQGTFTSDLSKYLDSARAEDFVKWLEST-OH
Compound 11;

(SEQ ID NO: 13)
Hy-HSQGTFTSDYSKYLD-Aib-ARAEDFVKWLEST-OH
Compound 12;

(SEQ ID NO: 14)
Hy-HSQGTFTSDYSKYLDSARAEDFVKWLES-OH
Compound 13;

(SEQ ID NO: 15)
Hy-HSQGTFTSDYSKYLDEARAEDFVKWLEST-OH
Compound 14;

(SEQ ID NO: 16)
Hy-HSQGTFTSDYSKYLD-Aib-ARAESFVKWLEST-OH
Compound 15;

(SEQ ID NO: 17)
Hy-HSQGTFTSDYSKYLESARAESFVKWLEST-OH
Compound 16;

(SEQ ID NO: 18)
Hy-HSQGTFTSDYSKYLDLARAEDFVKWLEST-OH
Compound 17;

(SEQ ID NO: 19)
Hy-HSQGTFTSDYSKYLDKRRAEDFVSWLEST-OH
Compound 18;

(SEQ ID NO: 20)
Hy-HSQGTFTSDYSKYLDVARAESFVKWLEST-OH
Compound 19;

(SEQ ID NO: 21)
Hy-HAQGTFTSDYSKYLD-Aib-ARAESFVKWLEST-OH
Compound 20;

(SEQ ID NO: 22)
Hy-HSQGTFTSDYSKYLD-Aib-ARAEEFVKWLEST-OH
Compound 21;

(SEQ ID NO: 23)
Hy-HSQ-DAla-TFTSDYSKYLD-Aib-ARAESFVKWLEST-OH
Compound 22;

(SEQ ID NO: 24)
Hy-HSQGTFTSDVSKYLD-Aib-ARAESFVKWLEST-OH
Compound 23;

(SEQ ID NO: 25)
Hy-HS-[Dab(Ac)]-GTFTSDYSKYLD-Aib-ARAESFVKWLEST-NH₂
Compound 24;

(SEQ ID NO: 26)
Hy-HSQGTFTSDYSKYLD-Aib-RRAESFVKWLEST-OH
Compound 25;

(SEQ ID NO: 27)
Hy-HS-[Gln(Me)]-GTFTSDYSKYLD-Aib-ARAESFVKWLEST-OH
Compound 26;

(SEQ ID NO: 28)
Hy-HSQGTFTSDYSKYLDEARAKSFVEWLEKT-OH
Compound 27;

(SEQ ID NO: 29)
Hy-HSQGTFTSDYSKYLDEARAKSFVEWLEST-OH
Compound 28;

(SEQ ID NO: 30)
Hy-HSQGTFTSDYSKYLD-Aib-ARAKSFVEWLEKT-OH
Compound 29;

(SEQ ID NO: 31)
Hy-HSQGTFTSDYSKYLD-Aib-ARAESFVKWLESA-OH
Compound 30;

(SEQ ID NO: 32)
Hy-HSQGTFTSDYSKYLD-Aib-ARAESFVKWLEST-NH₂
Compound 31;

(SEQ ID NO: 33)
Hy-HS-[Dab(Ac)]-GTFTSDYSKYLD-Aib-ARAESFVKWLEST-OH
Compound 32;

(SEQ ID NO: 34)
Hy-HSQGTFTSDYSKYLD-Aib-ARAEEFVSWLEKT-OH
Compound 33;

(SEQ ID NO: 35)
Hy-HSQGTFTSDYSKYLD-Aib-ARAEKFVEWLEST-OH
Compound 34;

(SEQ ID NO: 36)
Hy-HSQGTFTSDYSKYLD-Aib-ARAEEFVAWLEST-OH
Compound 35;

(SEQ ID NO: 37)
Hy-HSQGTFTSDYSKYLD-Aib-ARAEEFVKWLEET-OH
Compound 36;
```

-continued (SEQ ID NO: 38)
Hy-HSQGTFTSDYSKYLE-Aib-ARAEEFVKWLEST-OH
Compound 37;

(SEQ ID NO: 39)
Hy-HSHGTFTSDYSKYLD-Aib-ARAEEFVKWLEST-NH2
Compound 38;

(SEQ ID NO: 40)
Hy-HS-[Dab(Ac)]-GTFTSDYSKYLD-Aib-ARAEEFVKWLEST-OH
Compound 39;

(SEQ ID NO: 40)
Hy-HS-[Dab(Ac)]-GTFTSDYSKYLD-Aib-ARAEEFVKWLEST-NH$_2$
Compound 40;

(SEQ ID NO: 41)
Hy-HS-[Dap(Ac)]-GTFTSDYSKYLD-Aib-ARAEEFVKWLEST-NH$_2$
Compound 41;

and pharmaceutically acceptable salts and solvates thereof.

Each of the latter specific compounds (peptides), and pharmaceutically acceptable salts and solvates thereof, of the invention further constitutes an individual embodiment of the invention. Thus, in one embodiment the compound of the invention is (SEQ ID NO: 2)
Hy-HSQGTFTSDYSKYLDSARAESFVKWLEST-OH or a pharmaceutically acceptable salt or solvate thereof.
In another embodiment the compound of the invention is (SEQ ID NO: 3)
Hy-HSQGTFTSDYSKYLDSARAEDFVKWLEET-OH or a pharmaceutically acceptable salt or solvate thereof.
In another embodiment the compound of the invention is (SEQ ID NO: 4)
Hy-HSQGTFTSDYSKYLDKARAEDFVKWLEST-OH or a pharmaceutically acceptable salt or solvate thereof.
In another embodiment the compound of the invention is (SEQ ID NO: 5)
Hy-HSQGTFTSDYSKYLDSARAEDFVAWLEST-OH or a pharmaceutically acceptable salt or solvate thereof.
In another embodiment the compound of the invention is (SEQ ID NO: 6)
Hy-HSQGTFTSDYSKYLDEARAKDFVEWLEKT-OH or a pharmaceutically acceptable salt or solvate thereof.
In another embodiment the compound of the invention is (SEQ ID NO: 7)
Hy-HSQGTFTSDYSKYLDSARAEDFVEWLEST-OH or a pharmaceutically acceptable salt or solvate thereof.
In another embodiment the compound of the invention is (SEQ ID NO: 8)
Hy-HSQGTFTSDYSRYLESARAEDFVKWLEST-OH or a pharmaceutically acceptable salt or solvate thereof.
In another embodiment the compound of the invention is (SEQ ID NO: 9)
Hy-HSQGTFTSDYSKYLESARAEDFVKWLEST-OH or a pharmaceutically acceptable salt or solvate thereof.
In another embodiment the compound of the invention is (SEQ ID NO: 10)
Hy-HSQGTFTSDYSKYLDSARAEEFVKWLEST-OH or a pharmaceutically acceptable salt or solvate thereof.
In another embodiment the compound of the invention is (SEQ ID NO: 11)
Hy-HSQGTFTSDYSKYLDSARAEDFVSWLEST-OH or a pharmaceutically acceptable salt or solvate thereof.
In another embodiment the compound of the invention is (SEQ ID NO: 12)
Hy-HSQGTFTSDLSKYLDSARAEDFVKWLEST-OH or a pharmaceutically acceptable salt or solvate thereof.
In another embodiment the compound of the invention is (SEQ ID NO: 13)
Hy-HSQGTFTSDYSKYLD-Aib-ARAEDFVKWLEST-OH or a pharmaceutically acceptable salt or solvate thereof.
In another embodiment the compound of the invention is (SEQ ID NO: 14)
Hy-HSQGTFTSDYSKYLDSARAEDFVKWLES-OH or a pharmaceutically acceptable salt or solvate thereof.
In another embodiment the compound of the invention is (SEQ ID NO: 15)
Hy-HSQGTFTSDYSKYLDEARAEDFVKWLEST-OH or a pharmaceutically acceptable salt or solvate thereof.
In another embodiment the compound of the invention is (SEQ ID NO: 16)
Hy-HSQGTFTSDYSKYLD-Aib-ARAESFVKWLEST-OH or a pharmaceutically acceptable salt or solvate thereof.
In another embodiment the compound of the invention is (SEQ ID NO: 17)
Hy-HSQGTFTSDYSKYLESARAESFVKWLEST-OH or a pharmaceutically acceptable salt or solvate thereof.
In another embodiment the compound of the invention is (SEQ ID NO: 18)
Hy-HSQGTFTSDYSKYLDLARAEDFVKWLEST-OH or a pharmaceutically acceptable salt or solvate thereof.

In another embodiment the compound of the invention is

Hy-HSQGTFTSDYSKYLDKRRAEDFVSWLEST-OH (SEQ ID NO: 19)

or a pharmaceutically acceptable salt or solvate thereof.
In another embodiment the compound of the invention is Hy-HSQGTFTSDYSKYLDVARAESFVKWLEST-OH (SEQ ID NO: 20)

or a pharmaceutically acceptable salt or solvate thereof.
In another embodiment the compound of the invention is Hy-HAQGTFTSDYSKYLD-Aib-ARAESFVKWLEST-OH (SEQ ID NO: 21)

or a pharmaceutically acceptable salt or solvate thereof.
In another embodiment the compound of the invention is Hy-HSQGTFTSDYSKYLD-Aib-ARAEEFVKWLEST-OH (SEQ ID NO: 22)

or a pharmaceutically acceptable salt or solvate thereof.
In another embodiment the compound of the invention is Hy-HSQ-DAla-TFTSDYSKYLD-Aib-ARAESFVKWLEST-OH (SEQ ID NO: 23)

or a pharmaceutically acceptable salt or solvate thereof.
In another embodiment the compound of the invention is Hy-HSQGTFTSDVSKYLD-Aib-ARAESFVKWLEST-OH (SEQ ID NO: 24)

or a pharmaceutically acceptable salt or solvate thereof.
In another embodiment the compound of the invention is Hy-HS-[Dab(Ac)]-GTFTSDYSKYLD-Aib-ARAESFVKWLEST-NH$_2$ (SEQ ID NO: 25)

or a pharmaceutically acceptable salt or solvate thereof.
In another embodiment the compound of the invention is Hy-HSQGTFTSDYSKYLD-Aib-RRAESFVKWLEST-OH (SEQ ID NO: 26)

or a pharmaceutically acceptable salt or solvate thereof.
In another embodiment the compound of the invention is Hy-HS-[Gln(Me)]-GTFTSDYSKYLD-Aib-ARAESFVKWLEST-OH (SEQ ID NO: 27)

or a pharmaceutically acceptable salt or solvate thereof.
In another embodiment the compound of the invention is Hy-HSQGTFTSDYSKYLDEARAKSFVEWLEKT-OH (SEQ ID NO: 28)

or a pharmaceutically acceptable salt or solvate thereof.
In another embodiment the compound of the invention is Hy-HSQGTFTSDYSKYLDEARAKSFVEWLEST-OH (SEQ ID NO: 29)

or a pharmaceutically acceptable salt or solvate thereof.
In another embodiment the compound of the invention is Hy-HSQGTFTSDYSKYLD-Aib-ARAKSFVEWLEKT-OH (SEQ ID NO: 30)

or a pharmaceutically acceptable salt or solvate thereof.
In another embodiment the compound of the invention is Hy-HSQGTFTSDYSKYLD-Aib-ARAESFVKWLESA-OH (SEQ ID NO: 31)

or a pharmaceutically acceptable salt or solvate thereof.
In another embodiment the compound of the invention is Hy-HSQGTFTSDYSKYLD-Aib-ARAESFVKWLEST-NH$_2$ (SEQ ID NO: 32)

or a pharmaceutically acceptable salt or solvate thereof.
In another embodiment the compound of the invention is Hy-HS-[Dab(Ac)]-GTFTSDYSKYLD-Aib-ARAESFVKWLEST-OH (SEQ ID NO: 33)

or a pharmaceutically acceptable salt or solvate thereof.
In another embodiment the compound of the invention is Hy-HSQGTFTSDYSKYLD-Aib-ARAEEFVSWLEKT-OH (SEQ ID NO: 34)

or a pharmaceutically acceptable salt or solvate thereof.
In another embodiment the compound of the invention is Hy-HSQGTFTSDYSKYLD-Aib-ARAEKFVEWLEST-OH (SEQ ID NO: 35)

or a pharmaceutically acceptable salt or solvate thereof.
In another embodiment the compound of the invention is Hy-HSQGTFTSDYSKYLD-Aib-ARAEEFVAWLEST-OH (SEQ ID NO: 36)

or a pharmaceutically acceptable salt or solvate thereof.
In another embodiment the compound of the invention is Hy-HSQGTFTSDYSKYLD-Aib-ARAEEFVKWLEET-OH (SEQ ID NO: 37)

or a pharmaceutically acceptable salt or solvate thereof.
In another embodiment the compound of the invention is Hy-HSQGTFTSDYSKYLE-Aib-ARAEEFVKWLEST-OH (SEQ ID NO: 38)

or a pharmaceutically acceptable salt or solvate thereof.

In yet another embodiment the compound of the invention is

Hy-HSHGTFTSDYSKYLD-Aib-ARAEEFVKWLEST-NH$_2$ (SEQ ID NO: 39)

or a pharmaceutically acceptable salt or solvate thereof. In another embodiment the compound of the invention is Hy-HS-[Dab(Ac)]-GTFTSDYSKYLD-Aib-ARAEEFVKWLEST-OH (SEQ ID NO: 40)

or a pharmaceutically acceptable salt or solvate thereof. In another embodiment the compound of the invention is Hy-HS-[Dab(Ac)]-GTFTSDYSKYLD-Aib-ARAEEFVKWLEST-NH$_2$ (SEQ ID NO: 40)

or a pharmaceutically acceptable salt or solvate thereof. In another embodiment the compound of the invention is Hy-HS-[Dap(Ac)]-GTFTSDYSKYLD-Aib-ARAEEFVKWLEST-NH$_2$ (SEQ ID NO: 41)

or a pharmaceutically acceptable salt or solvate thereof.

Compounds of the invention may have one or more intramolecular bridges within the peptide sequence. Each such bridge is formed between the side-chains of two amino acid residues in the sequence which are typically separated by three other amino acid residues (i.e. between a side-chain of amino acid A and a side-chain of amino acid A+4).

For example, such a bridge may be formed between the side-chains of amino acid residue pairs 12 and 16, 16 and 20, 20 and 24, or 24 and 28. The two side-chains in question may be linked to one another through ionic interactions, or via covalent bonds. Thus, such pairs of amino acid residues may for example contain oppositely charged side-chains capable of forming a salt bridge or resulting in an ionic interaction. In such cases, one of the amino acid residues in question may, for example, be Glu or Asp, while the other may, for example, be Lys or Arg. Pairing of Lys and Glu or Lys and Asp may also lead to formation of a lactam ring.

Pharmaceutical Compositions

In some embodiments, the present invention relates to pharmaceutical compositions comprising a compound (or a pharmaceutically acceptable salt or solvate thereof) of the invention and a pharmaceutically acceptable carrier. Such pharmaceutical compositions may be prepared by conventional techniques, e.g. as described in Remington: *The Science and Practice of Pharmacy*, 19$^{th}$ edition, 1995.

Certain embodiments of liquid pharmaceutical compositions of the invention may comprise a compound of the invention present in a concentration from about 0.01 mg/ml to about 25 mg/ml, such as from about 1 mg/ml to about 10 mg/ml, e.g. from about 1 mg/ml to about 5 mg/ml. In some embodiments, the composition has a pH from 2.0 to 10.0. A pharmaceutical composition of the invention may further comprise a buffer system, preservative(s), isotonicity agent(s), chelating stabilizer(s) and/or surfactant(s). Particularly useful embodiments of liquid pharmaceutical compositions of the invention are aqueous compositions, i.e. compositions comprising water. Such compositions may be in the form of an aqueous solution or an aqueous suspension. Preferred embodiments of aqueous pharmaceutical compositions of the invention are aqueous solutions. In the context of the invention the term "aqueous composition" will normally refer to a composition comprising at least 50% by weight (50% w/w) of water. Likewise, the term "aqueous solution" will normally refer to a solution comprising at least 50% w/w of water, and the term "aqueous suspension" to a suspension comprising at least 50% w/w of water.

In some embodiments, a pharmaceutical composition of the invention comprises an aqueous solution of a compound (or a pharmaceutically acceptable salt or solvate thereof) of the invention present at a concentration of from 0.1 mg/ml or above, together with a buffer, the composition having a pH from about 2.0 to about 10.0, such as a pH from about 6.0 to about 8.5, e.g. from about 6.5 to about 8.5, such as from about 7.0 to about 8.5, or from about 6.5 to about 8.0.

In other embodiments of a pharmaceutical composition of the invention, the pH of the composition is a pH selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.8, 9.9, and 10.0. The pH of the composition may be at least 1 pH unit from (i.e., higher or lower than) the isoelectric point of the constituent compound of the invention, such as at least 2 pH units from (i.e., higher or lower than) the isoelectric point of the glucagon analogue compound of the invention.

In further embodiments of buffer-containing pharmaceutical compositions of the invention, the buffer or buffer substance is selected from the group consisting of: acetate buffers (e.g. sodium acetate), sodium carbonate, citrates (e.g. sodium citrate), glycylglycine, histidine, glycine, lysine, arginine, phosphates (e.g. chosen among sodium dihydrogen phosphate, disodium hydrogen phosphate and trisodium phosphate), TRIS (i.e., tris(hydroxymethyl)aminomethane), HEPES (i.e., 4-(2-hydroxyethyl)-1-piperazine-ethanesulfonic acid), BICINE (i.e., N,N-bis(2-hydroxyethyl)glycine), and TRICINE (i.e., N-[tris(hydroxymethyl)methyl]glycine), as well as succinate, malate, maleate, fumarate, tartrate, and aspartate buffers, and mixtures thereof.

In further embodiments of pharmaceutical compositions of the invention, the composition comprises a pharmaceutically acceptable preservative. Relevant preservatives include preservatives selected from the group consisting of: phenol, o-cresol, m-cresol, p-cresol, methyl p-hydroxybenzoate, ethyl p-hydroxybenzoate, propyl p-hydroxybenzoate, butyl p-hydroxybenzoate, 2-phenoxyethanol, 2-phenylethanol, benzyl alcohol, ethanol, chlorobutanol, thiomerosal, bronopol, benzoic acid, imidurea, chlorhexidine, sodium dehydroacetate, chlorocresol, benzethonium chloride, chlorphenesine [i.e. 3-(p-chlorphenoxy)propane-1,2-diol] and mixtures thereof. The preservative may be present in a concentration of from 0.1 mg/ml to 30 mg/ml, such as from 0.1 mg/ml to 20 mg/ml (e.g. from 0.1 mg/ml to 5 mg/ml, or from 5 mg/ml to 10 mg/ml, or from 10 mg/ml to 20 mg/ml) in the final liquid composition. The use of a preservative in pharmaceutical compositions is well known to the skilled worker. In this connection, reference may be made to Remington: *The Science and Practice of Pharmacy*, 19$^{th}$ edition, 1995.

In further embodiments, a pharmaceutical composition of the invention comprises an isotonicity agent (i.e., a pharmaceutically acceptable agent which is included in the composition for the purpose of rendering the composition isotonic). In some embodiments, the composition is administered to a subject by injection. Relevant isotonicity agents include agents selected from the group consisting of: salts (e.g., sodium chloride), sugars and sugar alcohols, amino acids (including glycine, arginine, lysine, isoleucine, aspartic acid, tryptophan and threonine), alditols (including glycerol, propyleneglycol (i.e. 1,2-propanediol), 1,3-propanediol and 1,3-butanediol), polyethylene glycols (including PEG400) and mixtures thereof. Suitable sugars include mono-, di- and polysaccharides, and water-soluble glucans, such as fructose, glucose, mannose, sorbose, xylose, maltose, lactose, sucrose, trehalose, dextran, pullulan, dextrin, cyclodextrin, soluble starch, hydroxyethyl starch and carboxymethylcellulose sodium salt. In some embodiments sucrose may be employed. Suitable sugar alcohols include hydroxylated $C_4$-$C_8$ hydrocarbons, including mannitol, sorbitol, inositol, galacititol, dulcitol, xylitol and arabitol. In some embodiments mannitol may be employed. The sugars or sugar alcohols mentioned above may be used individually or in combination. There is no fixed limit to the amount of isotonicity agent used, as long as it is soluble in the liquid formulation, establishes isotonicity and does not adversely effect the stability of the composition. The concentration of isotonicity agent (e.g. sugar or sugar alcohol) in the final liquid composition may be, e.g., from about 1 mg/ml to about 150 mg/ml, such as from 1 mg/ml to 50 mg/ml. In particular embodiments, the concentration may be from 1 mg/ml to 7 mg/ml, or from 8 mg/ml to 24 mg/ml, or from 25 mg/ml to 50 mg/ml. The use of an isotonicity agent in pharmaceutical compositions is well known to the skilled person. In this connection, reference may be made to Remington: *The Science and Practice of Pharmacy,* $19^{th}$ edition, 1995.

In further embodiments of pharmaceutical compositions of the invention, the composition comprises a chelating agent. Relevant chelating agents include salts of ethylenediaminetetraacetic acid (EDTA), citric acid or aspartic acid, and mixtures thereof. The chelating agent may suitably be present in the final liquid composition in a concentration of from 0.1 mg/ml to 5 mg/ml, such as from 0.1 mg/ml to 2 mg/ml, or from 2 mg/ml to 5 mg/ml. The use of a chelating agent in pharmaceutical compositions is well-known to the skilled worker. In this connection, reference may be made to Remington: *The Science and Practice of Pharmacy,* $19^{th}$ edition, 1995.

In further embodiments of pharmaceutical compositions of the invention, the composition comprises a stabilizer. The use of a stabilizer in pharmaceutical compositions is well-known to the skilled worker, and in this connection reference may be made to Remington: *The Science and Practice of Pharmacy,* $19^{th}$ edition, 1995. Particularly useful pharmaceutical compositions of the invention are stabilized liquid compositions with therapeutically active components that include a compound of the invention (e.g., a peptide of the invention) that may otherwise possibly exhibit aggregate formation during storage in a liquid medium. In this context, "aggregate formation" refers to physical interactions between the peptide molecules that result in formation of larger assemblies that undergo some degree of visible precipitation from the solution. As used herein, "during storage in a liquid medium" refers to the storage of a liquid composition that, once prepared, is not necessarily immediately administered to a subject. Instead, following preparation, it may be packaged for storage, either in a liquid form, in a frozen state, or in a dried form for later reconstitution into a liquid form or other form suitable for administration to a subject. As used herein, "dried form" refers to an initially liquid pharmaceutical composition or formulation that has been dried by freeze-drying (i.e., lyophilization), by spray-drying or by air-drying. Aggregate formation by a peptide during storage of a liquid pharmaceutical composition thereof can adversely affect biological activity of the peptide in question, resulting in a loss of therapeutic efficacy of the pharmaceutical composition. Furthermore, aggregate formation may cause other problems, such as blockage of tubing, membranes, or pumps if such a peptide-containing pharmaceutical composition is administered using an infusion system. Thus, peptides of the invention may be beneficial in overcoming these problems.

Examples of stabilizers appropriate for incorporation in pharmaceutical compositions of the invention include, but are not limited to, the following: amino acids in their free base form or salt form, e.g. amino acids carrying a charged side chain, such as arginine, lysine, aspartic acid or glutamic acid, or amino acids such as glycine or methionine (in that incorporation of methionine may additionally inhibit oxidation of methionine residues in peptides comprising at least one methionine residue susceptible to such oxidation); certain polymers (e.g., polyethylene glycols (such as PEG 3350), polyvinylalcohol (PVA), polyvinylpyrrolidone (PVP), and carboxy-/hydroxycellulose and derivatives thereof); cyclodextrins; sulfur-containing substances (such as monothioglycerol, thioglycolic acid and 2-methylthioethanol); and surfactants (such as non-ionic surfactants, including non-ionic surfactants of the Poloxamer or Polysorbate (Tween) types. The use of a surfactant in pharmaceutical compositions is well known to the skilled worker. In this connection, reference may be made to Remington: *The Science and Practice of Pharmacy,* $19^{th}$ edition, 1995.

Additional types of constituents may also be present in pharmaceutical compositions of the present invention. Non-limiting examples of classes of such constituents include wetting agents, emulsifiers, antioxidants, bulking agents, oleaginous vehicles and proteins (e.g., human serum albumin or gelatin).

Pharmaceutical compositions of the invention may be administered to a patient in need of such treatment at various sites, for example administration at sites which bypass absorption, such as in an artery or vein or in the heart, and at sites which involve absorption, such as in the skin, under the skin, in a muscle or in the abdomen. More generally, administration of pharmaceutical compositions according to the invention may be by a variety of routes of administration, such as or example parenteral, epidermal, dermal or transdermal routes. In some embodiments, other routes such as lingual, sublingual, buccal, oral, vaginal or rectal may be useful.

Compositions of the invention may be administered in various dosage forms, for example solutions, suspensions or emulsions, and are useful in the formulation of controlled-, sustained-, protracted-, retarded- or slow-release drug delivery systems. More specifically, but not exclusively, pharmaceutical compositions of the invention are useful in connection with parenteral controlled-release and sustained-release systems, well known to those skilled in the art. General reference may be made in this connection to *Handbook of Pharmaceutical Controlled Release* (Wise, D. L., ed., Marcel Dekker, New York, 2000) and *Drugs and the Pharmaceutical Sciences* vol. 99: *Protein Formulation and Delivery* (MacNally, E. J., ed., Marcel Dekker, New York, 2000).

Parenteral administration (of a liquid pharmaceutical composition of the invention) may be performed, for example, by subcutaneous, intramuscular, intraperitoneal or intravenous injection by means of a syringe, suitably a pen-like syringe. Alternatively, parenteral administration can take place by means of an infusion pump, e.g. in the form of a device or system borne by a subject or patient and comprising a reservoir containing a liquid composition of the invention and an infusion pump for delivery/administration of the composition to the subject or patient, or in the form of a corresponding miniaturized device suitable for implantation within the body of the subject or patient.

The term "stabilized composition" as employed herein refers to a composition having increased physical stability, increased chemical stability or increased physical and chemical stability. The term "physical stability" as used herein refers to a measure of the tendency of a peptide (e.g., a compound of the invention) to form soluble or insoluble aggregates of the peptide, for example as a result of exposure of the peptide to stresses and/or interaction with interfaces and surfaces that are destabilizing, such as hydrophobic surfaces and interfaces. Physical stability of aqueous peptide compositions may be evaluated by means of visual inspection and/or turbidity measurements after exposing the composition, filled in suitable containers (e.g. cartridges or vials), to mechanical/physical stress (e.g. agitation) at different temperatures for various time periods. A composition may be classified as physically unstable with respect to peptide aggregation when it exhibits visual turbidity. Alternatively, the turbidity of a composition can be evaluated by simple turbidity measurements well-known to the skilled person. Physical stability of an aqueous peptide composition can also be evaluated by using an agent that functions as a spectroscopic probe of the conformational status of the peptide. The probe is preferably a small molecule that preferentially binds to a non-native conformer of the peptide. One example of such a small-molecular spectroscopic probe is Thioflavin T, which is a fluorescent dye that has been widely used for the detection of amyloid fibrils. In the presence of fibrils, and perhaps also other peptide configurations, Thioflavin T gives rise to a new excitation maximum at about 450 nm and enhanced emission at about 482 nm when bound to a fibril form of a peptide. Unbound Thioflavin T is essentially non-fluorescent at the wavelengths in question.

The term "chemical stability" as used herein refers to stability of a peptide with respect to covalent chemical changes in the peptide structure that lead to formation of chemical degradation products with potentially lower biological potency and/or potentially increased immunogenicity compared to the native peptide structure. Various chemical degradation products can be formed, depending on the type and detailed nature of the native peptide and the environment to which the peptide is exposed. In practise, elimination of chemical degradation in peptide compositions in general cannot be avoided completely, and the formation of increasing amounts of chemical degradation products is often seen during storage and use of such compositions, as is well-known to the person skilled in the art. Many peptides are susceptible to a degradation process in which the side-chain amide group in glutaminyl or asparaginyl residues is hydrolysed to form a free carboxylic acid. Other degradation pathways involve formation of high-molecular-weight transformation products in which two or more peptide molecules become covalently bound to each other through transamidation and/or disulfide interactions, leading to formation of covalently bound oligomer and polymer degradation products (see, e.g., *Stability of Protein Pharmaceuticals*, Ahern. T. J. and Manning M. C., Plenum Press, New York 1992). Oxidation (e.g., of methionine residues) is another form of chemical degradation of peptides. The chemical stability of a peptide composition may be evaluated by measuring the amounts of chemical degradation products at various timepoints after exposure to different environmental conditions (for example, formation of degradation products may often be accelerated by increasing temperature). The amount of each individual degradation product may be determined by separation of the degradation products on the basis of molecular size and/or charge using various chromatographic techniques (e.g. SEC-HPLC and/or RP-HPLC).

The chemical instability of glucagon per se at low pH is mainly due to isomerisation and cleavage of aspartic acid residues, deamidation of glutamine residues and oxidation of methionine. Generally speaking, Asn and Gln deamidation occurs at high pH, with significant rates at physiological pH around pH 7.4 via a cyclic imide ring intermediate which can open to create L-Asp and L-isoAsp or L-Glu and L-isoGlu, respectively. The cyclic imide ring intermediate also may lead to the formation of small amounts of the corresponding D-isomers, indicating a slow racemisation of the cyclic imide.

At pH values below physiological pH, the rate of deamidation of Asn and Gln is reduced, but the rate of formation of a cyclic imide from Asp and Glu, and hence isomerisation, increases with decreasing pH. Cyclic imide formation is greatest between pH 4 and pH 6. Formation of the cyclic imide intermediate can also result in cleavage of the peptide sequence.

As outlined above, a "stabilized composition" may thus refer to a composition with increased physical stability, or increased chemical stability, or increased physical and chemical stability. In general, a composition should be stable during use and storage (in compliance with recommended use and storage conditions) at least until the specified expiration date is reached.

In certain embodiments of pharmaceutical compositions of the invention (e.g., liquid compositions) the composition is stable for at least 2 weeks of usage and for at least 6 months of storage. In further embodiments, the composition is stable for at least 2 weeks of usage and for at least one year of storage. In still further embodiments, the composition is stable for at least 2 weeks of usage and for at least two years of storage. In other embodiments, the composition is stable for at least 4 weeks of usage and for at least two years of storage, or even for at least 4 weeks of usage and for more than 3 years of storage. Particularly useful embodiments of such pharmaceutical compositions of the invention are stable for at least 6 weeks of usage and for at least 3 years of storage. In this regard, the term "usage" for the purposes of this paragraph refers to taking the pharmaceutical composition out of storage for the purpose of employing the composition for therapeutic purposes, and thereby subjecting it to varying ambient conditions (conditions of light, dark, temperature, agitation etc.), whilst the term "storage" for the purposes of this paragraph refers to storage under non-agitated conditions in a refrigerator or freezer at a temperature not exceeding about 5° C. The skilled worker will understand the typical range of usage and storage conditions that these pharmaceutical compositions may be subjected to.

Nucleic Acids, Expression Vectors and Host Cells

The invention provides a nucleic acid molecule (e.g. an isolated nucleic acid molecule) encoding a compound of the invention, or the peptide sequence Z of a compound of the invention.

It will be understood that a compound of the invention, or peptide sequence Z, can typically only be encoded by a nucleic acid sequence when the peptide sequence Z comprises only naturally occurring amino acids, i.e. the twenty amino acids which occur naturally in mammalian proteins.

As discussed above, the invention relates, inter alia, to an expression vector comprising a nucleic acid construct sequence of the invention, optionally in combination with one or more sequences to direct its expression, and to a host cell containing an expression vector of the invention. Preferably the host cell is capable of expressing and secreting a compound of the invention or a compound having the peptide sequence Z of a compound of the invention. In some embodiments, the present invention provides a method of producing a compound of the invention, wherein the method comprises culturing host cells of the invention under conditions suitable for expressing the compound and purifying the compound thus produced. Alternatively, the method may comprise expressing a compound having the peptide sequence Z of a compound of the invention, and subsequently modifying the N- and/or C-terminus to obtain a compound of the invention. The invention further provides (i) a nucleic acid of the invention, (ii) an expression vector of the invention, and (iii) a host cell capable of expressing and optionally secreting a compound of the invention, for use in a method of medical treatment. The nucleic acid, expression vector and host cells may be used for treatment of any of the disorders described herein which may be treated with a compound of the invention themselves. References to a pharmaceutical composition comprising a compound of the invention, administration of a compound of the invention, or any therapeutic use thereof, should therefore be construed to encompass the equivalent use of a nucleic acid, expression vector or host cell of the invention, except where the context demands otherwise.

Peptide Synthesis

Peptides of the present invention may be manufactured by standard chemical synthetic methods, or by using recombinant expression systems, or by any other suitable state-of-the-art method. Thus, the glucagon analogues may be synthesized in a number of ways, including, inter alia, methods comprising:

(a) synthesizing the peptide by means of solid-phase or liquid-phase methodology, either stepwise or by fragment assembly, and isolating and purifying the final peptide product; or (b) expressing a nucleic acid construct that encodes the peptide in a host cell, and recovering the expression product from the host cell culture; or (c) effecting cell-free in vitro expression of a nucleic acid construct that encodes the peptide, and recovering the expression product;

or employing any combination of methods as in (a), (b) and (c) to obtain fragments of the peptide, subsequently joining (e.g., ligating) the fragments to obtain the complete peptide, and recovering the peptide.

It may be preferable to synthesize compounds of the invention by means of solid-phase or liquid-phase peptide synthesis, the methodology of which is well known to persons of ordinary skill in the art of peptide synthesis. Reference may also be made in this respect to, for example, WO 98/11125 and Fields, G. B. et al., 2002, *"Principles and practice of solid-phase peptide synthesis"*. In: *Synthetic Peptides* (2nd Edition), and examples provided therein.

For recombinant expression, nucleic acid constructs of the invention may be inserted in suitable vectors to form cloning or expression vectors carrying the nucleic acid constructs of the invention (such vectors also constituting aspects of the present invention). The vectors can, depending on purpose and type of application, be in the form of plasmids, phages, cosmids, mini-chromosomes, or viral, but naked DNA which is only expressed transiently in certain cells may also be an important vector. Preferred cloning and expression vectors (plasmid vectors) of the invention are capable of replication, thereby enabling high copy-numbers for the purposes of high-level expression or high-level replication for subsequent cloning.

In general, an expression vector may comprise the following features in the 5'3' direction and operably linked: a promoter for driving expression of the nucleic acid fragment of the invention, optionally a nucleic acid sequence encoding a leader peptide enabling secretion (to the extracellular phase or, where applicable, into the periplasma), the nucleic acid fragment encoding the peptide of the invention, and optionally a nucleic acid sequence encoding a terminator. The expression vector also may comprise additional features such as selectable markers and origins of replication. When operating with expression vectors in producer strains or cell lines, it may be preferred that the vector is capable of integrating into the host cell genome. The skilled person will be familiar with suitable vectors, and will be able to design one according to the specific requirements in question.

Vectors of the invention may be used to transform host cells to produce compounds of the invention. Such transformed cells, which also constitute embodiments of the invention, can be cultured cells or cell lines used for propagation of the nucleic acid fragments and vectors of the invention, or may be used for recombinant production of the peptides of the invention.

In some embodiments, the transformed cells of the invention are micro-organisms such as bacteria (e.g., species of *Escherichia* (e.g., *E. coli*), *Bacillus* (e.g., *B. subtilis*), *Salmonella* or *Mycobacterium* (preferably non-pathogenic, e.g., *M. bovis* BCG)), yeasts (e.g., *Saccharomyces cerevisiae* or *Pichia pastoris*), or protozoans. Alternatively, the transformed cells may be derived from a multicellular organism, e.g., the cells may be fungal cells, insect cells, algal cells, plant cells, or animal cells such as mammalian cells. For the purposes of cloning and/or optimised expression, the transformed cell may be capable of replicating the nucleic acid construct of the invention. Cells expressing the nucleic acid constructs are useful embodiments of the invention, and may be used for small-scale or large-scale preparation of peptides of the invention.

When producing a peptide of the invention by means of transformed cells, it will be convenient, although not essential, that the expression product is secreted into the culture medium.

Efficacy

The compounds of the invention have glucagon agonist activity.

Binding of the relevant compounds to glucagon (Glu or GCG) receptors may be used as an indication of agonist activity. In alternative embodiments, a biological assay which measures intracellular signalling caused by binding of the compound to the receptor may also be used. For example, activation of the glucagon receptor by a glucagon receptor agonist will stimulate cellular cyclic AMP (cAMP) formation. Thus, production of cAMP in suitable cells expressing the receptor can be used to monitor receptor activity.

The skilled person will be aware of suitable assay formats, and examples are provided below.

By way of example, the assay may employ the human glucagon receptor (GCG-R) having primary accession number GI:4503947 (NP_000151.1) or having primary accession number P47871. The skilled worker will understand in this connection that when sequences of precursor proteins are referred to, assays may make use of the mature protein lacking the signal sequence. Suitable cells are typically mammalian cells, e.g. rodent or primate cells, e.g. rat, mouse or hamster cells, or human cells such as HEK293 cells. They may express their endogenous glucagon receptor or may have been engineered to express glucagon receptor (e.g. having the human sequence referred to above). The assay may be performed using the materials and under the conditions set out in Example 3.

$EC_{50}$ values may be used as a numerical measure of agonist potency at a given receptor, the $EC_{50}$ value being a measure of the concentration of a compound required to achieve half of that compound's maximal activity towards the receptor in question in a particular assay.

Therapeutic Uses

Compounds (and pharmaceutically acceptable salts or solvates thereof) of the invention, as well as pharmaceutical compositions of the invention, may be useful in the treatment or prevention of a variety of conditions or disorders. Optionally, the compounds (and pharmaceutically acceptable salts or solvates thereof) may be used in combination with one or more additional therapeutically active substances. Relevant therapeutic uses thus include: treatment or prevention of hypoglycaemia (both acute and chronic), type 2 diabetes (including disease progression in type 2 diabetes), impaired glucose tolerance, type 1 diabetes, obesity (including diseases or states related to overweight or obesity), coronary heart disease, atherosclerosis, hypertension, dyslipidemia, hepatic steatosis, β-blocker poisoning, insulinoma and Von Gierkes disease; preventing a subject from becoming overweight; reducing body weight; decreasing food intake; increasing energy expenditure; delaying progression from impaired glucose tolerance (IGT) to type 2 diabetes; delaying progression from type 2 diabetes to insulin-requiring diabetes; regulating appetite or inducing satiety (including treatment of bulimia and treatment of binge-eating); and preventing weight regain after successful weight loss. As a general principle, compounds (and pharmaceutically acceptable salts or solvates thereof) of the invention, as well as pharmaceutical compositions of the invention, may be useful to control blood glucose levels.

Among forms of hypoglycaemia capable of treatment or prevention in accordance with the invention are diabetic hypoglycaemia (including acute insulin-induced hypoglycaemia), non-diabetic hypoglycaemia, reactive hypoglycaemia, fasting hypoglycaemia, drug-induced hypoglycaemia, alcohol-induced hypoglycaemia, gastric bypass-induced hypoglycaemia, and hypoglycaemia occurring during pregnancy.

Additional applications of compounds (and pharmaceutically acceptable salts or solvates thereof) of the invention, and pharmaceutical compositions of the invention, include uses as a smooth-muscle relaxant (spasmolytic agent) in connection with imaging procedures (e.g., X-ray, computer tomography (CT) or magnetic resonance (MR) imaging), such as imaging of the abdominal region.

Combination Therapy

As already indicated above, treatment with a compound (or pharmaceutically acceptable salt or solvate thereof) according to the present invention may take place in combination with one or more other pharmacologically active substances or agents, e.g., selected from antidiabetic agents, antiobesity agents, appetite-regulating agents, antihypertensive agents, agents for the treatment and/or prevention of complications resulting from or associated with diabetes, and agents for the treatment and/or prevention of complications and disorders resulting from or associated with obesity. In the present context, the expression "antidiabetic agent" includes compounds for the treatment and/or prophylaxis of insulin resistance and diseases wherein insulin resistance is the pathophysiological mechanism.

Examples of such pharmacologically active substances are insulin and insulin analogues, GLP-1 agonists, sulfonylureas (e.g. tolbutamide, glibenclamide, glipizide and gliclazide), biguanides (e.g. metformin), meglitinides, glucosidase inhibitors (e.g. acarbose), glucagon antagonists, dipeptidyl peptidase IV (DPP-IV) inhibitors, inhibitors of hepatic enzymes involved in stimulation of gluconeogenesis and/or glycogenolysis, glucose uptake modulators, thiazolidinediones such as troglitazone and ciglitazone, compounds modifying the lipid metabolism such as antihyperlipidemic agents (e.g. HMG CoA inhibitors (statins)), compounds lowering food intake, RXR agonists and agents acting on the ATP-dependent potassium channel of the β-cells, e.g. glibenclamide, glipizide, gliclazide and repaglinide; cholestyramine, colestipol, clofibrate, gemfibrozil, lovastatin, pravastatin, simvastatin, probucol, dextrothyroxine, neteglinide, repaglinide; β-blockers, such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers, such as nifedipine, felodipine, nicardipine, isradipine, nimodipine, diltiazem and verapamil, and α-blockers, such as doxazosin, urapidil, prazosin and terazosin; CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, (33 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline reuptake inhibitors, mixed serotonin and noradrenergic compounds, 5HT (serotonin) agonists, bombesin agonists, galanin antagonists, growth hormone, growth hormone releasing compounds, TRH (thyrotropin releasing hormone) agonists, UCP 2 or 3 (uncoupling protein 2 or 3) modulators, leptin agonists, DA agonists (e.g. bromocryptin, doprexin), lipase/amylase inhibitors, RXR (retinoid X receptor) modulators, TR β agonists, and histamine H3 antagonists.

Any suitable combination of a compound or compounds according to the invention with one or more of the above-mentioned compounds, and optionally one or more further pharmacologically active substances, is within the scope of the present invention.

Experimental Methods

Abbreviations employed in the following are as follows:

COMU: 1-[(1-(cyano-2-ethoxy-2-oxoethylideneaminooxy)-dimethylamino-morpholinomethylene)]methanaminium hexafluorophosphate DCM: dichloromethane DMF: N,N-dimethylformamide DIPEA: diisopropylethylamine EtOH: ethanol Et$_2$O: diethyl ether HATU: N-[(dimethylamino)-1H-1,2,3-triazol[4,5-b]pyridine-1-ylmethylene]-N-methylmethanaminium hexafluorophosphate N-oxide HPLC: high-performance liquid chromatography IBMX: 3-isobutyl-1-methylxanthine MeCN: acetonitrile
MS: mass spectroscopy
PBS phosphate-buffered saline
RP: reverse phase
TFA: trifluoroacetic acid
TIS: triisopropylsilane General Synthesis Procedure for Glucagon Analogues Solid phase peptide synthesis (SPPS) was performed on a microwave assisted synthesizer using standard Fmoc strategy in DMF on a polystyrene resin (TentaGel S Ram or Tentagel S PHB-Thr(tBu)). HATU or COMU was used as coupling reagent together with DIPEA as base. Piperidine (20% in DMF) was used for deprotection. Pseudoprolines: Fmoc-Phe-Thr($\Psi$ Me, Me pro)-OH, Fmoc-Asp-Ser($\Psi$, Me, Me pro)-OH and Fmoc-Glu-Ser($\Psi$, Me, Me pro)-OH (purchased from NovaBiochem) were used where applicable. Human glucagon was likewise synthesized and purified using synthesis methodology and purification procedures as described herein.

Cleavage:

The crude peptide was cleaved from the resin by treatment with 95/2.5/2.5% (v/v) TFA/TIS/water at room temperature for 2 h. Most of the TFA was removed at reduced pressure, and the crude peptide was precipitated and washed with diethyl ether and allowed to dry at ambient temperature.

Peptide Purification

The crude peptides were purified by standard RP HPLC with a gradient of buffer A (0.1% aqueous TFA) and buffer B (aqueous solution containing 0.1% TFA and 90% MeCN). Fractions were analysed by analytical HPLC and MS, and relevant fractions were pooled and lyophilised.

The peptides were further purified by preparative RP HPLC using a gradient of buffer A' (0.1% aqueous formic acid) and buffer B' (aqueous solution containing 0.1% formic acid and 90% MeCN). TFA was added to the collected fractions prior to lyophilisation. The final product was characterised by analytical HPLC and MS.

Analytical HPLC Method

The peptides were analyzed by an analytical HPLC method using a gradient of buffer A' (see above) and buffer B' (see above).

Example 1

Synthesis of Compound 7

Compound 7 (SEQ ID NO: 8) was synthesized on a CEM Liberty Peptide Synthesizer using Tentagel S PHB-Thr(tBu) resin (1.13 g, 0.24 mmol/g), COMU as coupling reagent, DMF as the solvent, and Fmoc-chemistry as described above. Pseudoprolines Fmoc-Phe-Thr($\Psi$ Me, Me pro)-OH (in position 6/7) and Fmoc-Glu-Ser($\Psi$, Me, Me pro)-OH (in position 15/16) were used in the sequence.

The peptide was cleaved from the resin as described above, and the purification was performed on a Gemini-NX column (5 cm, C18, 10 micron) with a 35 ml/min flow of a mixture of buffer A (see above) and buffer B (see above). The product was eluted with a linear gradient of 20-50% buffer B over 47 min, and relevant fractions were analyzed by analytical HPLC and MS. Pooled fractions were lyophilized and redissolved in water prior to further purification on a Gemini-NX column (2.12×25 cm, C18 (110 A); 10 micron) with a 10 ml/min flow of a mixture of buffer A' (see above) and buffer B' (see above). The product was eluted with a linear gradient of 5-40% buffer B' over 47 min, and relevant fractions were analyzed by analytical HPLC and MS. TFA was added to the pooled fractions and they were lyophilized to give 112 mg. The purity was 99% as determined by analytical HPLC (see above), and the monoisotopic mass was 3409.55 Da as determined by MS (calc. 3409.58 Da).

Example 2

Generation of Cell Line Expressing Human Glucagon Receptor

The cDNA encoding the human glucagon receptor (Glucagon-R) (primary accession number P47871) was cloned from the cDNA clone BC104854 (MGC:132514/IMAGE:8143857). The DNA encoding the Glucagon-R was amplified by PCR using primers encoding terminal restriction sites for subcloning. The 5'-end primers additionally encoded a near-Kozak consensus sequence to ensure efficient translation. The fidelity of the DNA encoding the Glucagon-R was confirmed by DNA sequencing. The PCR products encoding the Glucagon-R were subcloned into a mammalian expression vector containing a neomycin (G418) resistance marker. The mammalian expression vector encoding the Glucagon-R was transfected into HEK293 cells by a standard calcium phosphate transfection method. 48 hr after transfection, cells were seeded for limited dilution cloning and selected with 1 mg/ml G418 in the culture medium. Three weeks later twelve surviving colonies of Glucagon-R-expressing cells were picked, propagated and tested in the Glucagon-R efficacy assay as described below. One Glucagon-R expressing clone was chosen for compound profiling.

Example 3

Glucagon Receptor Assay

HEK293 cells expressing the human Glucagon-R were seeded at 60,000 cells per well in 96-well microtiter plates coated with 0.01% poly-L-lysine, and grown for 1 day in culture in 100 µl growth medium. For analyses of the induction of cAMP by the Glucagon-R we used the AlphaScreen® cAMP Assay Kit from Perkin Elmer, according to manufacturer instructions. On the day of analysis, growth medium was removed and the cells were washed once with 200 ml of the included Assay buffer with IBMX. Cells were incubated in 100 ml Assay buffer/IBMX containing increasing concentrations of test peptides for 15 min at 37° C. Then the peptides/Assay buffer was removed and cells were lysed by addition of 80 ml Lysis buffer pr. well and incubation for at least 10 min at room temperature. From each well 10 ml cell lysate was transferred to a 384-well OptiPlate and mixed with Donor and Acceptor beads and incubated for 1 h at room temperature. The cAMP content was measured on an Envision plate reader. $EC_{50}$ and relative efficacies compared to reference compound (glucagon) were estimated by computer-aided curve fitting.

Example 4

Solubility Assessment

A stock solution of the test peptide (2 mg/ml; determined by measurement of the absorption of the solution at 280 nm, and using the theoretical extension coefficient based on the content of tryptophan and tyrosine in the peptide) in demineralized water adjusted to pH 2.5 with HCl was prepared, and aliquots were diluted 1:1 in 100 mM acetate buffer (pH 4.0) and 100 mM phosphate buffer (pH 7.5), respectively, and loaded in a standard flat-bottom, non-sterile 96-well UV Microplate. The absorbance of samples (single samples, n=1) at 280 and 325 nm was measured in an absorbance-based plate reader, which was preheated to ambient temperature. The turbidity absorbance criterion for a peptide solubility of ≥1 mg/ml was an absorbance at 325 nm≤0.02 absorbance units (which is 5 to 6 times the standard deviation of 8 buffer samples in a plate).

Numerous compounds of the invention exhibit a solubility of ≥1 mg/ml in the pH range from 4 to 7.5, more specifically at pH 4 and pH 5 (e.g. in acetate buffer), and at pH 6, pH 7 and pH 7.5 (e.g. in phosphate buffer).

Example 5

Assessment of Physical Stability

Aggregation in the form of fibril formation was detected using the amyloid-specific dye Thioflavin T (ThT), which is frequently employed to demonstrate the presence of fibrils in solution (see, e.g., Groenning, M., *J. Chem. Biol.* 3(1) (2010), pp. 1-18; Groenning et al., *J. Struct. Biol.* 158 (2007) pp. 358-369; and Levine, H., III, *Protein Sci.* 2 (1993) pp. 404-410) All test peptides were dissolved in demineralized water adjusted to pH 2.5 with HCl, at ambient temperature. A solution containing 1 mg/ml of peptide, 40 µM ThT and 50 mM phosphate buffer, pH 7.5, was loaded in a 96-well black fluorescence plate (clear bottom) in triplicate. Data were collected at fixed intervals of 10 min, each preceded by 300 s of automixing (agitation), over a period of 96 hours at 40° C. The entire experiment was repeated, but without agitation. Physical stability, expressed as lag-time of fibril formation (in hours), was defined as the intersection between two linear regressions representing the initial stable phase and the growth phase.

Example 6

Chemical Stability Assessment

Stock solutions of each test peptide (1 mg/ml; determined by measurement of the absorption of the solution at 280 nm, and using the theoretical extension coefficient based on the content of tryptophan and tyrosine in the peptide) in 50 mM acetate buffer (pH 4.0) and in 50 mM phosphate buffer (pH 7.5), respectively, were prepared. Samples were placed in glass vials and incubated at 40° C. The samples were analysed by reverse-phase HPLC on a C18 column with gradient elution using an acetonitrile/trifluoroacetic acid/water eluent system. The area-percentage (area-%) of the main peak after incubation time T=t (relative to time T=0) was detected by UV spectrometry at 220 nm.

The purity was first determined as follows:

Purity(area-%)=(area of main peak/total area of all peaks)×100.

The purity was then normalized between time points by setting purity at time 0 (T=0) to 100 for each pH value for a given peptide, as follows:

Normalised area-% at time t(T=t)=[area-%(T=t)/area-%(T=0)]×100.

The in vitro activity results (expressed as $EC_{50}$ values) and the results of the assessment of solubility are summarized in Table 1 (below), and the physical and chemical stability assessment results are summarized in Table 2 (below). Normalized purity values in Table 2 were determined after 14 days of incubation.

Example 7

Acute Glucose Release

The effect of Compound 14 of the invention (doses of 20 and 60 nmol/kg body weight, respectively) on acute glucose release in euglycemic male Sprague-Dawley rats (Taconic, Lille Skensved, Denmark, 9-10 weeks old) in comparison with that of native human glucagon (dose 20 nmol/kg) was investigated. The rats were fasted for 5 hours prior to dosing. The animals (n=6/group) were injected once subcutaneously (SC) with vehicle (PBS, pH 7.4), test compound or glucagon. Blood samples were collected from the tail vein prior to dosing (t=0) and every 15 minutes for 2 hours thereafter using 5 µl capillary tubes. Animals were anaesthetized (with a standard mixture of hypnorm/dormicum) during the experiment to ensure stable baseline blood glucose levels. Blood glucose concentrations were determined using a Biosen Glucose Analyser (EKF-diagnostic GmbH, Germany). The data are summarized in FIG. 1.

Example 8

Pharmacokinetics

A comparative pharmacokinetic evaluation of native human glucagon and a representative compound of the present invention in mice, rats and dogs was made. The two compounds exhibited similar pharmacokinetic characteristics, e.g. with respect to half-life (t½) and volume of distribution.

TABLE 1

$EC_{50}$ and solubility data for compounds of the invention

| Compound No. | Seq. ID No. | GCG-R $EC_{50}$ in vitro [nM]# | Solubility pH 7.5 |
| --- | --- | --- | --- |
| Glucagon | 1 | 0.013 | <1 mg/mL |
| 1 | 2 | 0.064 | ≥1 mg/mL |
| 2 | 3 | 0.18 | ≥1 mg/mL |
| 3 | 4 | 0.030 | ≥1 mg/mL |
| 4 | 5 | 0.34 | ≥1 mg/mL |
| 5 | 6 | 0.17 | ≥1 mg/mL |
| 6 | 7 | 1.0 | ≥1 mg/mL |
| 7 | 8 | 0.93 | ≥1 mg/mL |
| 8 | 9 | 0.38 | ≥1 mg/mL |
| 9 | 10 | 0.030 | ≥1 mg/mL |
| 10 | 11 | 0.32 | ≥1 mg/mL |
| 11 | 12 | 0.11 | ≥1 mg/mL |
| 12 | 13 | 0.030 | ≥1 mg/mL |
| 13 | 14 | 0.070 | ≥1 mg/mL |
| 14 | 15 | 0.15 | ≥1 mg/mL |
| 15 | 16 | 0.030 | ≥1 mg/mL |
| 16 | 17 | 0.39 | ≥1 mg/mL |
| 17 | 18 | 0.029 | ≥1 mg/mL |
| 18 | 19 | 0.026 | ≥1 mg/mL |
| 19 | 20 | 0.054 | ≥1 mg/mL |
| 20 | 21 | 0.24 | ≥1 mg/mL |
| 21 | 22 | 0.0095 | ≥1 mg/mL |
| 22 | 23 | 0.024 | ≥1 mg/mL |
| 23 | 24 | 0.16 | ≥1 mg/mL |
| 24 | 25 | 0.0078 | ≥1 mg/mL |
| 25 | 26 | 0.0066 | ≥1 mg/mL |
| 26 | 27 | 0.0069 | ≥1 mg/mL |
| 27 | 28 | 0.063 | ≥1 mg/mL |
| 28 | 29 | 0.035 | ≥1 mg/mL |
| 29 | 30 | 0.023 | ≥1 mg/mL |
| 30 | 31 | 0.016 | ≥1 mg/mL |
| 31 | 32 | 0.0072 | ≥1 mg/mL |

TABLE 1-continued

EC$_{50}$ and solubility data for compounds of the invention

| Compound No. | Seq. ID No. | GCG-R EC$_{50}$ in vitro [nM]# | Solubility pH 7.5 |
|---|---|---|---|
| 32 | 33 | 0.0093 | ≥1 mg/mL |
| 33 | 34 | 0.044 | ≥1 mg/mL |
| 34 | 35 | 0.028 | ≥1 mg/mL |
| 35 | 36 | 0.014 | ≥1 mg/mL |
| 36 | 37 | 0.010 | ≥1 mg/mL |
| 37 | 38 | 0.094 | ≥1 mg/mL |
| 38 | 39 | 0.0047 | ≥1 mg/mL |
| 39 | 40 | 0.0044 | ≥1 mg/mL |
| 40 | 40 | 0.0035 | ≥1 mg/mL |
| 41 | 41 | 0.0038 | ≥1 mg/mL |

All values quoted to two significant figures

TABLE 2

Physical and chemical stability data for compounds of the invention.

| Compound No. | Seq. ID No: | Normalized purity pH 4.0 after 14 days [%] | Normalized purity pH 7.5 after 14 days [%] | Physical Stability at pH 7.5 [hrs:mins] (non-agitated) | Physical Stability at pH 7.5 [hrs:mins] (agitated) |
|---|---|---|---|---|---|
| 1 | 2 | N/A | N/A | 05:18 ± 00:23 | 01:49 ± 00:10 |
| 2 | 3 | 83.5 | 86.2 | FND | FND |
| 3 | 4 | 85.0 | 86.5 | FND | 72:50 ± 06:16 |
| 4 | 5 | 80.5 | 84.6 | FND | FND |
| 5 | 6 | 91.8 | 89.6 | FND | FND |
| 8 | 9 | Not performed | Not performed | 85 | 57:02 ± 0:43 |
| 9 | 10 | Not performed | Not performed | onset | 53:20 ± 05:46 |
| 10 | 11 | Not performed | Not performed | FND | FND |
| 11 | 12 | 78.6 | 89.9 | FND | FND |
| 12 | 13 | 86.8 | 90.8 | FND | FND |
| 13 | 14 | 84.6 | 88.8 | FND | 80:10 ± 14:54 |
| 14 | 15 | 89.5 | 92.4 | FND | FND |
| 15 | 16 | 89.1 | 95.1 | FND | FND |
| 16 | 17 | 89.1 | Not performed | 12:57 ± 00:02 | Not performed |
| 17 | 18 | 89.9 | 88.3 | 62 ± 4 | 41:33 ± 04:18 |
| 18 | 19 | Not performed | Not performed | 15:04 ± 00:41 | 03:48 ± 00:06 |
| 19 | 20 | Not performed | Not performed | onset | Not performed |
| 20 | 21 | Not performed | Not performed | FND | FND |
| 21 | 22 | 89.8 | 93.5 | FND | FND |
| 22 | 23 | 91.1 | 95.3 | FND | FND |
| 23 | 24 | Not performed | Not performed | FND | FND |
| 24 | 25 | 92.8 | 94.4 | FND | FND |
| 25 | 26 | 93.8 | 89.8 | FND | FND |
| 26 | 27 | 90 | 93.9 | FND | FND |
| 27 | 28 | Not performed | Not performed | 46:20 ± 04:43 | 18:00 ± 04:00 |
| 28 | 29 | Not performed | Not performed | 08:33 ± 00:05 | 02:20 ± 00:17 |
| 29 | 30 | 91 | 91.6 | FND | FND |
| 30 | 31 | 88.6 | 91.4 | FND | FND |
| 31 | 32 | 93.1 | 91.7 | FND | FND |
| 32 | 33 | 91.2 | 96.3 | FND | FND |
| 33 | 34 | Not performed | Not performed | Not performed | FND |
| 34 | 35 | Not performed | Not performed | Not performed | FND |
| 35 | 36 | Not performed | Not performed | Not performed | FND |
| 36 | 37 | Not performed | Not performed | Not performed | FND |
| 37 | 38 | Not performed | Not performed | Not performed | FND |
| 38 | 39 | Not performed | Not performed | Not performed | FND |

*FND = fibrillation not detected

The invention claimed is:

1. A method of treating a subject suffering from hypoglycaemia comprising administering a therapeutically effective amount of the compound:

(SEQ ID NO: 22)
Hy-HSQGTFTSDYSKYLD-Aib-ARAEEFVKWLEST-OH, or pharmaceutically acceptable salt thereof to the subject.

2. The method of claim 1, wherein the hypoglycaemia is selected from the group consisting of:
diabetic hypoglycaemia, acute insulin-induced hypoglycaemia, non-diabetic hypoglycaemia, reactive hypoglycaemia, fasting hypoglycaemia, drug-induced hypoglycaemia, alcohol-induced hypoglycaemia, gastric bypass-induced hypoglycaemia, and hypoglycaemia occurring during pregnancy.

3. The method of claim 2, wherein the hypoglycaemia is diabetic hypoglycaemia.

4. The method of claim 2, wherein the hypoglycaemia is acute insulin-induced hypoglycaemia.

5. The method of claim 2, wherein the hypoglycaemia is non-diabetic hypoglycaemia.

6. The method of claim 2, wherein the hypoglycaemia is reactive hypoglycaemia.

7. The method of claim 2, wherein the hypoglycaemia is fasting hypoglycaemia.

8. The method of claim 2, wherein the hypoglycaemia is drug-induced hypoglycaemia.

9. The method of claim 2, wherein the hypoglycaemia is alcohol-induced hypoglycaemia.

10. The method of claim 2, wherein the hypoglycaemia is gastric bypass-induced hypoglycaemia.

11. The method of claim 2, wherein the hypoglycaemia is hypoglycaemia occurring during pregnancy.

* * * * *

UNITED STATES PATENT AND TRADEMARK OFFICE
CERTIFICATE OF CORRECTION

PATENT NO. : 11,795,204 B2
APPLICATION NO. : 16/566992
DATED : October 24, 2023
INVENTOR(S) : Ditte Riber et al.

Page 1 of 1

It is certified that error appears in the above-identified patent and that said Letters Patent is hereby corrected as shown below:

On the Title Page

Under the Related U.S. Application Data, add item --(30) Foreign Application Priority Data
Jun. 14, 2013 (DK) ... PA 2013 00360--.

Signed and Sealed this
Twenty-fifth Day of June, 2024

Katherine Kelly Vidal
*Director of the United States Patent and Trademark Office*